(12) United States Patent
Gainer

(10) Patent No.: US 11,147,859 B2
(45) Date of Patent: *Oct. 19, 2021

(54) DIFFUSION ENHANCING COMPOUNDS AND THEIR USE ALONE OR WITH THROMBOLYTICS

(71) Applicant: Diffusion Pharmaceuticals LLC, Charlottesville, VA (US)

(72) Inventor: John L. Gainer, Charlottesville, VA (US)

(73) Assignee: DIFFUSION PHARMACEUTICALS LLC, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/193,762

(22) Filed: Nov. 16, 2018

(65) Prior Publication Data

US 2019/0083584 A1   Mar. 21, 2019

Related U.S. Application Data

(63) Continuation of application No. 12/801,726, filed on Jun. 22, 2010, now Pat. No. 10,130,689.

(60) Provisional application No. 61/213,575, filed on Jun. 22, 2009.

(51) Int. Cl.
| | | |
|---|---|---|
| *A61K 38/48* | (2006.01) | |
| *A61K 31/203* | (2006.01) | |
| *A61P 9/10* | (2006.01) | |

(52) U.S. Cl.
CPC .......... *A61K 38/482* (2013.01); *A61K 31/203* (2013.01); *A61P 9/10* (2018.01)

(58) Field of Classification Search
CPC ........ A61K 38/482; A61K 31/203; A61P 9/10
USPC .......................................................... 514/183
See application file for complete search history.

(56) References Cited

U.S. PATENT DOCUMENTS

| | | |
|---|---|---|
| 2,175,843 A | 10/1939 | Kuhn et al. |
| 2,948,748 A | 8/1960 | Guex et al. |
| 3,489,806 A | 1/1970 | Gutmann et al. |
| 3,687,990 A | 8/1972 | Gutmann et al. |
| 3,788,468 A | 1/1974 | Gainer |
| 3,853,933 A | 12/1974 | Siciliano |
| 3,853,993 A | 12/1974 | Gainer |
| 3,965,261 A | 6/1976 | Gainer |
| 3,975,519 A | 8/1976 | Gainer |
| 4,009,270 A | 2/1977 | Gainer, Jr. |
| 4,038,144 A | 7/1977 | Gainer |
| 4,046,880 A | 9/1977 | Gainer |
| 4,070,460 A | 1/1978 | Gainer, Jr. |

(Continued)

FOREIGN PATENT DOCUMENTS

| | | |
|---|---|---|
| AU | 2003215396 | 9/2003 |
| CA | 2477245 | 9/2003 |

(Continued)

OTHER PUBLICATIONS

ACLS Training Center Stroke Assessment, pp. 1-2, 2016.*

(Continued)

*Primary Examiner* — Deborah D Carr
(74) *Attorney, Agent, or Firm* — Hoxie & Associates LLC

(57) ABSTRACT

The subject invention relates to diffusion enhancing compounds and their use alone or with thrombolytic agents for the treatment of disorders resulting from the formation of a thrombus such as a myocardial infarction or stroke.

21 Claims, 5 Drawing Sheets

(56) References Cited

U.S. PATENT DOCUMENTS

| | | |
|---|---|---|
| 4,099,270 A | 7/1978 | Jabour |
| 4,105,855 A | 8/1978 | Schulz et al. |
| 4,176,179 A | 11/1979 | Gainer |
| 4,216,211 A | 8/1980 | Francis |
| 4,699,664 A | 10/1987 | Hettiarachchy et al. |
| 4,727,064 A | 2/1988 | Pitha |
| 5,032,613 A | 7/1991 | Watson |
| 5,053,240 A | 10/1991 | Todd, Jr. |
| 5,107,030 A | 4/1992 | Babler |
| 5,424,407 A | 6/1995 | Tanaka et al. |
| 5,472,946 A | 12/1995 | Peck et al. |
| 5,811,119 A | 9/1998 | Mehta et al. |
| 5,817,332 A | 10/1998 | Urtti et al. |
| 6,060,511 A | 5/2000 | Gainer |
| 6,150,561 A | 11/2000 | Kreienbuhl et al. |
| 6,235,311 B1 | 5/2001 | Ullah et al. |
| 6,555,526 B2 | 4/2003 | Matsuo et al. |
| 6,855,734 B2 | 2/2005 | Messadek |
| 7,145,025 B2 | 12/2006 | Lockwood et al. |
| 7,317,008 B2 | 1/2008 | Lockwood et al. |
| 7,351,844 B2 | 4/2008 | Gainer et al. |
| 7,446,101 B1 | 11/2008 | Madhavi et al. |
| 7,521,584 B2 | 4/2009 | Lockwood et al. |
| 7,759,506 B2 | 7/2010 | Gainer et al. |
| 7,887,840 B2 | 2/2011 | Curatolo et al. |
| 7,919,527 B2 | 4/2011 | Gainer et al. |
| 8,017,653 B2 | 9/2011 | Gainer et al. |
| 8,030,350 B2 | 10/2011 | Gainer et al. |
| 8,206,751 B2 | 6/2012 | Gainer |
| 8,269,027 B2 | 9/2012 | Gainer et al. |
| 8,293,804 B2 | 10/2012 | Gainer |
| 8,901,174 B2 | 12/2014 | Gainer |
| 8,974,822 B2 | 3/2015 | Gainer et al. |
| 9,604,899 B2 | 3/2017 | Gainer et al. |
| 9,950,067 B2 | 4/2018 | Gainer et al. |
| 10,016,384 B2 | 7/2018 | Gainer et al. |
| 10,130,689 B2 | 11/2018 | Gainer |
| 2002/0055486 A1 | 5/2002 | Matsuo et al. |
| 2002/0065320 A1 | 5/2002 | Messadek |
| 2003/0072801 A1 | 4/2003 | Curatolo et al. |
| 2003/0180281 A1 | 9/2003 | Bott et al. |
| 2003/0180282 A1* | 9/2003 | Serebruany .......... A61K 31/445 424/94.64 |
| 2003/0186931 A1 | 10/2003 | Matsuo et al. |
| 2004/0014725 A1 | 1/2004 | Gainer et al. |
| 2004/0109920 A1 | 6/2004 | Reuscher et al. |
| 2004/0116729 A1 | 6/2004 | Gainer et al. |
| 2004/0162329 A1 | 8/2004 | Lockwood et al. |
| 2005/0113372 A1 | 5/2005 | Lockwood et al. |
| 2006/0194973 A1 | 8/2006 | Gainer et al. |
| 2006/0233877 A1 | 10/2006 | Messadek et al. |
| 2006/0276372 A1 | 12/2006 | Lockwood et al. |
| 2006/0281724 A1 | 12/2006 | Loria |
| 2007/0088248 A1 | 4/2007 | Glenn |
| 2007/0135521 A1 | 6/2007 | Okada et al. |
| 2007/0161610 A1 | 7/2007 | Gainer et al. |
| 2007/0166339 A1 | 7/2007 | Gupta |
| 2007/0203353 A1 | 8/2007 | Gainer et al. |
| 2008/0113031 A1 | 5/2008 | Moodley et al. |
| 2008/0255246 A1* | 10/2008 | Gainer .................. A61K 31/015 514/763 |
| 2009/0110746 A1 | 4/2009 | Gainer |
| 2009/0118227 A1 | 5/2009 | Jouni et al. |
| 2009/0169586 A1 | 7/2009 | Tracton |
| 2009/0176287 A1 | 7/2009 | Schmidt-Dannert et al. |
| 2010/0137436 A1 | 6/2010 | Gainer et al. |
| 2010/0322918 A1 | 12/2010 | Gainer |
| 2011/0196038 A1 | 8/2011 | Gainer et al. |
| 2011/0294884 A1 | 12/2011 | Gainer et al. |
| 2011/0300213 A1 | 12/2011 | Gainer et al. |
| 2012/0035256 A1 | 2/2012 | Gainer |
| 2012/0095099 A1 | 4/2012 | Gainer et al. |
| 2013/0018014 A1 | 1/2013 | Gainer |
| 2014/0051759 A1 | 2/2014 | Gainer et al. |
| 2015/0352068 A1 | 12/2015 | Gainer et al. |
| 2016/0199490 A1 | 7/2016 | Gainer et al. |
| 2017/0202798 A1 | 7/2017 | Gainer et al. |
| 2018/0271979 A1 | 9/2018 | Gainer et al. |
| 2019/0038586 A1 | 2/2019 | Gainer et al. |
| 2019/0083439 A1 | 3/2019 | Gainer |

FOREIGN PATENT DOCUMENTS

| | | |
|---|---|---|
| CA | 2524573 A1 | 11/2004 |
| CH | 522 572 | 10/1969 |
| CN | 1215723 | 5/1999 |
| CN | 1671643 | 9/2005 |
| CN | 1708480 | 12/2005 |
| CN | 1243120 | 2/2006 |
| CN | 1842512 | 10/2006 |
| CN | 1997365 | 7/2007 |
| CN | 10-1180257 | 5/2008 |
| CN | 100033 | 11/2016 |
| EP | 0 612 815 | 8/1994 |
| EP | 0 908 449 | 9/1998 |
| EP | 1 192 947 | 4/2002 |
| EP | 1 621 199 A1 | 2/2006 |
| EP | 1 667 954 | 6/2006 |
| GB | 2 353 934 | 3/2001 |
| JP | 45-014114 | 5/1970 |
| JP | 63-059831 | 3/1983 |
| JP | 61-254161 | 11/1986 |
| JP | 63-222114 | 9/1988 |
| JP | 1-238536 | 9/1989 |
| JP | 02-121934 | 5/1990 |
| JP | A 03-056412 | 3/1991 |
| JP | A 04-264020 | 9/1992 |
| JP | 05-032531 | 2/1993 |
| JP | A 05-178765 | 7/1993 |
| JP | 06-248193 | 9/1994 |
| JP | 07-023736 | 1/1995 |
| JP | 07-223960 | 8/1995 |
| JP | A 07-291854 | 11/1995 |
| JP | 09-512552 | 12/1997 |
| JP | 10-502388 | 3/1998 |
| JP | 11-19261 | 1/1999 |
| JP | 11-029466 | 2/1999 |
| JP | A-11-180901 | 7/1999 |
| JP | 11-209642 | 8/1999 |
| JP | 2000-007570 | 1/2000 |
| JP | 2001-511135 | 8/2001 |
| JP | 2001-302517 | 10/2001 |
| JP | 2002-524535 | 8/2002 |
| JP | 2002-538113 | 11/2002 |
| JP | 2003-026607 | 1/2003 |
| JP | 2003-201238 | 7/2003 |
| JP | 2005-053841 | 3/2005 |
| JP | 2005-518453 | 6/2005 |
| JP | 2006-525270 | 11/2006 |
| JP | 2006-342108 | 12/2006 |
| JP | 2007-522076 | 8/2007 |
| JP | 2010-106029 | 12/2009 |
| JP | 2010-090151 | 4/2010 |
| JP | 2010-229137 | 5/2010 |
| KR | 1999-0036861 | 5/1999 |
| KR | 10-2006-0020616 | 3/2006 |
| KR | 10-2010-0016396 | 2/2010 |
| RU | 2107496 | 3/1998 |
| RU | 2226096 | 3/2004 |
| RU | 2256446 | 7/2005 |
| RU | 2265434 | 12/2005 |
| WO | WO 1992/015544 | 9/1992 |
| WO | WO 1995/000130 | 1/1995 |
| WO | WO 1998/014183 | 4/1998 |
| WO | WO 1998/032421 | 7/1998 |
| WO | WO 1999/015150 | 4/1999 |
| WO | WO 2000/015262 | 3/2000 |
| WO | WO 2001/013933 A2 | 3/2001 |
| WO | WO 2001/013933 A3 | 9/2002 |
| WO | WO 2003/059270 A2 | 7/2003 |
| WO | WO 2003/072734 | 9/2003 |
| WO | WO 2004/005353 | 1/2004 |
| WO | WO 2004/011423 | 2/2004 |
| WO | WO 2004/041284 A1 | 5/2004 |

(56) References Cited

FOREIGN PATENT DOCUMENTS

| | | |
|---|---|---|
| WO | WO 2004/048323 | 6/2004 |
| WO | WO 2004/049095 | 6/2004 |
| WO | WO 2004/091630 A1 | 10/2004 |
| WO | WO 2005/004854 | 1/2005 |
| WO | WO 2005/028411 | 3/2005 |
| WO | WO 2005/120495 | 12/2005 |
| WO | WO 2006/039685 | 4/2006 |
| WO | WO 2006/083780 A2 | 8/2006 |
| WO | WO 2006/093348 | 9/2006 |
| WO | WO 2006/104610 | 10/2006 |
| WO | WO 2007/072529 | 6/2007 |
| WO | WO 2008/014685 | 2/2008 |
| WO | WO 2008/027687 | 3/2008 |
| WO | WO 2008/102563 | 8/2008 |
| WO | WO 2008/135090 | 11/2008 |
| WO | WO 2008/136900 | 11/2008 |
| WO | WO 2009/058399 | 5/2009 |
| WO | WO 2009/111688 | 9/2009 |
| WO | WO 2010/151314 | 12/2010 |
| WO | WO 2011/152869 | 12/2011 |
| WO | WO 2017/165667 | 9/2017 |

OTHER PUBLICATIONS

U.S. Appl. No. 60/907,718, filed Apr. 13, 2007, Gainer, J.L.
U.S. Appl. No. 61/001,095, filed Oct. 31, 2007, Gainer, J.L., et al.
U.S. Appl. No. 61/350,804, filed Jun. 2, 2010, Gainer, J.L., et al.
U.S. Appl. No. 16/030,496, filed Jul. 9, 2018, Gainer, J.L., et al.
U.S. Appl. No. 16/087,993, filed Sep. 24, 2018, Gainer, J.L.
Ahmad, A.S. et al., "Neuroprotection by cretin in a hemiparkinsonian rat model," *Pharmacology Biochemistry and Behavior*, vol. 81, pp. 805-813, (2005).
Abusuev, A.A., "Clinical Course of Myocardial Infarction in Treatment with Perfluorane, in Perfluorocarbon Compounds in Experimental and Clinical Medicine," *Collected Works of the Russian Scientific Conference*, St. Petersburg, 2004, p. 12 (No English Translation Available.).
Bennett, M.H. et al., "Hyperbaric oxygen therapy for late radiation tissue injury (Review)," *The Cochrane Collaboration* Published by John Wiley & Sons, Ltd., Copyright 2009, Issue 2.
Boileau, T. W.-M., et al., "Bioavailability of all-trans and cis-Isomers of Lycopene," *Experimental Biology and Medicine*, vol. 227, pp. 914-919, (2002); http://ebm.sagepub.com/content/227/10/914.
Borisova, I.V. et al., "Renal and Neuroprotective Effects of Perfluorane in Induced Toxic Renal Injury in Rats," Medline.ru-Biomeditsinskii Zhurnal, vol. 5, Art. 16, pp. 136-139, (2004).
Britton, G. et al., "Isolation and Analysis," *Carotenoids*, vol. IA, pp. 103-107; p. 283, Birkhauser Verlag, Basel, (1995).
Broderick, J.P., et al., "Finding the Most Powerful Measures of the Effectiveness of Tissue Plasminogen Activator in the NINDS tPA Stroke Trial," *Stroke*, vol. 31, No. 10, pp. 2335-2341, (2000).
Brown, J. Martin, et al., "The Unique Physiology of Solid Tumors: Opportunities (and Problems) for Cancer Therapy," *Cancer Research*, vol. 58, pp. 1408-1416,(1998).
Buchta and Andree, "The Total Synthesis of trans-2,2-Bisdimethyl-crocetin-dimetyl ester and trans-Crocetin-dimethyl ester," *Naturwiss*, (1959).
Buchta, E. et al, "Eine Totalsynthese des „all"-trans-Crocetin-dimethylesters2", *Chemischte Berichte Jahrg.*, vol. 93, pp. 1349-1353, (1960).
Bui, Q-C et al., "The Efficacy of Hyperbaric Oxygen Therapy in the Treatment of Radiation-Induced Late Side Effects, " *Int. J. Radiation Oncology Biol. Phys.*, vol. 60, No. 3, pp. 871-878, (2004).
Burukhina, A.N. et al., "Experience of Using Perfluorane in Treating Acute Massive Hemorrhage in Obstetric Practice, in Collected Works of the 12th Scientific and Practical Conference of Physicians Topical Issues in Modern Medicine," *Novosibirsk*, Chapter 2, pp. 39-40, (2002).

Calvo, W. et al., "Time—and dose-related changes in the white matter of the rat brain after single doses of X rays," The British Journal of Radiology, vol. 61, pp. 1043-1052, (1988).
Cianci, P. "Hyperbaric therapy for radiation injury," *Radiation Injury, Advances in Management and Prevention* edited by J.L. Meyer, et al., pp. 98-109, (1999).
Clark, W.M., et al., "The rtPA (Alteplase) 0- to 6-Hour Acute Stroke Trial, Part A (A0276g): Results of a Double-Blind, Placebo-Controlled, Multicenter Study," *Stroke*, vol. 31, No. 4, pp. 311-816, (2000).
CMC Co. Ltd., published Pharmaceutical Formulation Strategies and New Technology, Mar. 31, 2007, first printing, p. 88.
Coppola, G.M., "Amberlyst-15, A Superior Acid Catalyst for the Cleavage of Actetals," Syn. Communications 1021 (1984).
Craw, M. and Lambert, C., "The Characterisation of the Triplet State of Crocetin, a Water Soluble Carotenoid, by Nanosecond Laser Flash Photolyses," *Photochemistry and Photobiology*, vol. 38, No. 2, pp. 241-243, (1983).
Chryssanthi, D.G., et al., "A New Validated SPE-HPLC Method for Monitoring Crocetin in Human Plasma—Application After Saffron Tea Consumption," Journal of Pharmaceutical and Biomedical Analysis, vol. 55, pp. 563-568, (2011); DOI: 10.1016/j.jpba.2011.02.018.
Cutright, D.E. et al., "Long-Term Effects of Radiation on the Vascularity of Rat Bone—Quantitative Measurements with a New Technique," Radiation Research, vol. 48, pp. 402-408 (1971).
Database Caplus, Chemical Abstracts Service, Columbus, Ohio, US, (1988), XP002317165 [JP 63 059831].
Database Caplus, Chemical Abstracts Service, Columbus, Ohio, US, (1993), XP002317166 [JP 05 032531].
Denninghoff, et al., "Retinal Imaging Techniques in Diabetes," *Diabetes Technology & Therapeutics*, vol. 2, No. 1, pp. 111-113 (2000).
Finney, J., et al., "Protection of the ischemic heart with DMSO alone or DMSO with hydrogen peroxide," *Annals of the New York Academy of Sciences*, vol. 141, No. I, pp. 231-241, (1967).
Gainer, J.L., et al., "Oxygen diffusion and atherosclerosis," *Atherosclerosis*, vol. 19, pp. 135-138, (1974).
Gainer, J.L. et al., "Using Excess Volume of Mixing to Correlate Diffusivities in Liquids," *Chem. Eng. Commun.*, vol. 15, pp. 323-329, (1982).
Gainer, J.L., et al., "The Effect of Crocetin on Hemorrhagic Shock in Rats," *Circulatory Shock*, vol. 41, pp. 1-7, (1993).
Gainer, J.L., "Altering Diffusivities in Dilute Polymeric and Biological Solutions," *Ind. Engr. Chem. Research*, vol. 33, pp. 2341-2344, (1994).
Gainer, J.L. et al., "The effect of trans sodium crocetinate (TSC) in a rat oleic acid model of acute lung injury," *Pulmonary Pharmacology & Therapeutics*, Academic Press, GB, vol. 18, No. 3, pp. 213-216, (2005), XP004737366.
Gainer, J. L., "Trans-Sodium Crocetinate for Treating Hypoxia/Ischemic," *Expert Opinion on Investigational Drugs*, vol. 17, No. 6, pp. 917-924, (2008).
Galinski, Erwin A., et al., "The Kosmotropic (Structure-Forming) Effect of Compensatory Solutes," *Comp. Biochem. Physiol.*, vol. 117A, No. 3, pp. 357-365, (1997).
General Information on Perfluorane, Medline.ru-Biomeditsinskii Zhurnal, vol. 5, Art. 16, pp. 68-69, (2004), www.medline.ru/public/art/tom5/art8-perf2.phtm (with English translation).
Ghandehari, K. et al., "Thrombolysis in stroke patients; Problems and limitations," *Iran Journal of Med. Sci.*, vol. 35, Issue 2, pp. 145-148, (2010).
Giassi, L.J. et al., "Trans Sodium Crocetinate Restores Blood Pressure, Heart Rate, and Plasma Lactate after Hemorrhagic Shock," *Journal of Trauma*, vol. 51, pp. 932-938, (2001).
Giassi, L.J., et al., "Trans Sodium Crocetinate for Hemorrhagic Shock: Effect of Time Delay in Initiating Therapy," *Shock*, vol. 18, No. 6, pp. 585-588, (2002).
Gibson, T.W. et al., "Sulfinic Acid Catalyzed Isomerization of Olefins," *J. Org. Chem.*, vol. 41, No. 5, pp. 791-793 (1976), XP002325593.
Gill, A.L. et al., "Hyperbaric oxygen: its uses, mechanisms of action and outcomes," *Q. J. Med.*, vol. 97, pp. 385-395, (2004).

(56) References Cited

OTHER PUBLICATIONS

Goldstick, T.K., Ph.D, "Diffusion of Oxygen in Protein Solutions," Dissertation, University of California, Berkeley, CA, pp. 13-28, (1966).
Gree, R. et al., "Fumaraldehyde Monodimethyl Acetal: An Easily Accessible and Versatile Intermediate," *Tetrahedron Letters*, vol. 27, No. 41, pp. 4983-4986, (1986).
Greenwood, T.W. et al., "Hyperbaric Oxygen and Wound Healing in Post-Irradiation Head and Neck Surgery," Brit. J. Surg., vol. 60, No. 5, pp. 394-397, (1973).
Group, N.r.—P.S.S., "Tissue Plasminogen Activator For Acute Ischemic Stroke," *The New England Journal of Medicine*, vol. 333, No. 24, pp. 1581-1587, (1995).
Holland, R.A.B. et al., "Kinetics of O2 Uptake and Release by Red Cells in Stopped-Flow Apparatus: Effects of unstirred Layer," *Respiration Physiology*, vol. 59, pp. 71-91, (1985).
Holloway, G.M., et al., "The carotenoid crocetin enhances pulmonary oxygenation," *The American Physiological Society*, pp. 683-686, Department of Chemical Engineering, and Dept. of Anesthesiology, School of Medicine, Univ. of VA, Charlotteville, Va, (1988).
Huxley, V.H., et al., "The Effect of the Red Cell Membrane and a Diffusion Boundary Layer on the Rate of Oxygen Uptake by Human Erythrocytes," *J. Physiol.*, vol. 316, pp. 75-83, (1981).
International Preliminary Examination Report on Patentability (IPRP) (Chapter 1) for PCT/US2003/005521, prepared Aug. 23, 2004.
International Preliminary Report on Patentability dated May 25, 2007 in PCT/US2003/026424; prepared May 10, 2007.
International Preliminary Report on Patentability for International Application No. PCT/US2006/006422 dated Aug. 28, 2007.
International Preliminary Report on Patentability dated Oct. 13, 2009 in International Application No. PCT/US2008/004708.
International Preliminary Report on Patentability for International Application No. PCT/US2008/012440 dated May 4, 2010.
International Preliminary Report on Patentability dated Jan. 12, 2012 in PCT/US2010/001794.
International Preliminary Report on Patentability (IPRP) (Chapter I) for PCT/US2011/000997, dated Dec. 4, 2012.
International Search Report and for International Application No. PCT/US2003/005521 dated Dec. 24, 2003.
International Search Report for International Application No. PCT/US2003/026424 dated Nov. 5, 2004.
International Search Report and Written Opinion for International Application No. PCT/US2006/006422 dated Oct. 19, 2006.
International Search Report and Written Opinion dated Jul. 22, 2008 for International Application No. PCT/US2008/004708.
International Search Report and Written Opinion for International Application No. PCT/US2008/012440 dated Mar. 25, 2009.
International Search Report and Written Opinion for International Application No. PCT/US2010/001794 dated Sep. 1, 2010.
International Search Report and Written Opinion for International Application No. PCT/US2011/000997 dated Sep. 9, 2011.
Ingall, T., "Stroke-Incidence, Mortality, Morbidity And Risk," *Journal of Insurance Medicine*, vol. 36, pp. 143-152, (2004).
Isler, O. et al., "Anwendung der Wittig-Reaktion zur Synthese von Estern des Bixins und Crocetins," *Helv. Chim. Acta*, vol. 40, No. 139, pp. 1242-1249, (1957); XP008042920.
Jansen, F.J.H.M., et al., "Synthesis and Characterization of All-E $(12,12'-^{13}C_2)$-, $(13,13'-^{13}C_2)$-, $(14,14'-^{13}C_2)$-, $(15,15'-^{13}C_2)$- and $(20,20'-^{13}C_2)$astaxanthin," *Recl. Trav. Chim. Pays-Bas*, vol. 113, p. 552-562, (1994).
Jiho, Inc., Design and Evaluation of Oral Formulation, pp. 337-339, (1995); No English Translation Available.
Johnson, M.E., et al., "Synergistic Effects of Chemical Enhancers and Therapeutic Ultrasound on Transdermal Drug Delivery," *Journal of Pharmaceutical Sciences*, vol. 85, No. 7, pp. 670-679, (1996).
Kalani, M., et al., "Hyperbaric Oxygen (HBO) Therapy in Treatment of Diabetic Foot Ulcers Long-term Follow-up," *Journal of Diabetes & Its Complications*, pp. 153-158, (2002).

Kamiryo, T. et al., "Histological Changes in the Normal Rat Brain After Gamma Irradiation," *Acta Neurochir (Wien)*, vol. 138, pp. 451-459, (1996).
Kamiryo, T. et al., "Radiosurgery-induced Microvascular Alterations Precede Necrosis of the Brain Neuropil," *Neurosurgery*, vol. 49, No. 2, pp. 409-415, (2001).
Kichev, G.S. et al., "Experience of Using Perfluorane in Treating Critical Conditions of Various Geneses," *Medline.ru-Biomeditsinskii Zhurnal*, vol. 5, Art. 53, pp. 175-177, (2004); No English Translation Available.
Koynova, R., et al., "Modulation of Lipid Phase Behavior by Kosmotropic and Chaotropic Solutes—Experiment and Thermodynamic Theory," *Eur Biophys J*, vol. 25, pp. 261-274, (1997).
Laidig, K.E. et al., "Altering Diffusivity in Biological Solutions through Modification of Solution Structure and Dynamics," *Journal of the American Chemical Society*, vol. 120, No. 36, pp. 9394-9395, (1998); XP002970835.
Lancrajan, I., et al., "Carotenoid incorporation into natural membranes from artificial carriers: liposomes and beta-cyclodextrins," *Chemistry and Physics of Lipids*, vol. 112, pp. 1-10, (2001); XP55044152.
Lang, A.E., et al., "Parkinson's Disease," *New England Journal of Medicine*, vol. 339, No. 15, pp. 1044-1053, (1998).
Lapchak, P.A., et al., "Neuroprotective Effects of the Spin Trap Agent Disodium-[(tert-butylimino)methyl]benzene-1,3-disulfonate N-Oxide (Generic NXY-059) in a Rabbit Small Clot Embolic Stroke Model: Combination Studies With the Thrombolytic Tissue Plasminogen Activator," *Stroke*, vol. 33, No. 5, pp. 1411-1415, (2002); DOI: 10.1161/01.STR.0000015346.00054.8B.
Lapchak, P.A., et al., "Comparison of Tenecteplase With Alteplase On Clinical Rating Scores Following Small Clot Embolic Strokes in Rabbits," *Experimental Neurology*, vol. 185, pp. 154-159, (2004); DOI: 10.1016/j.expneurol.2003.09.009.
Lapchak, P.A. et al., "Transcranial Infrared Laser Therapy Improves Clinical Rating Scores After Embolic Strokes in Rabbits," *Stroke*, vol. 35, No. 8, pp. 1985-1988, (2004); DOI: 10.1161/01.STR.0000131808.69640.b7.
Lapchak, P.A., "Memantime, an uncompetitive low affinity NMDA open-channel antagonist improves clinical rating scores in a multiple infarct embolic stroke model in rabbits," *Brain Research*, vol. 1088, No. 1 , pp. 141-147, (2006); DOI: 10.1016/j.brainres.2006.02.093.
Lapchak, P.A., et al., "Advances in Ischemic Stroke Treatment: Neuroprotective And Combination Therapies," *Expert Opin. Emerging Drugs*, vol. 12, No. 2, pp. 1-16, (2007); DOI: 10.1517/14728214.12.2.
Lapchak, P.A., "The *Phenylpropanoid* Micronutrient Chlorogenic Acid Improves Clinical Rating Scores in Rabbits Following Multiple Infarct Ischemic Strokes: Synergism With Tissue Plasminogen Activator," *Experimental Neurology*, vol. 205, No. 2, pp. 407-413, (2007); DOI: 10.1016/j.expneurol.2007.02.017.
Lapchak, P.A., et al., "Transcranial Near-Infrared Light Therapy Improves Motor Function Following Embolic Strokes In Rabbits: An Extended Therapeutic Window Study Using Continuous And Pulse Frequency Delivery Modes," *Neuroscience*, vol. 148, pp. 907-914, (2007); DOI: 10.1016/j.neuroscience.2007.07.002.
Lapchak, P.A., et al., "Therapeutic Window for Nonerythropoietic carbamylated-erythropoietin to Improve Motor Function Following Multiple Infarct Ischemic Strokes in New Zealand White Rabbits," *Brain Research*, vol. 1238, pp. 208-214, (2008); DOI: 10.1016/j.brainres.2008.08.017.
Lapchak, P.A., "Efficacy and Safety Profile of the Carotenoid Trans Sodium Crocetinate Administered to Rabbits Following Multiple Infarct Ischemic Strokes: A Combination Therapy Study with Tissue Plasminogen Activator," *Brain Research*, vol. 1309, pp. 136-145, (2010), XP-002686117; DOI: 10.1016/j.brainres.2009.10.067.
Letham, D.S., et al., "The Synthesis of Radioisotopically Labelled Zeatin," *Phytochemistry*, vol. 10, pp. 2077-2081, (1971).
Lever, M., et al., "Some Ways of Looking at Compensatory Kosmotropes and Different Water Environments," *Comparative Biochemistry and Physiology, Part A*, vol. 130, pp. 471-486, (2001).
Lide, D.R. Ph.D., "CRC Handbook of Chemistry and Physics," *CRC Press*, 79th Edition, Boca Raton, FL, pp. 6-181, (1998).

(56) References Cited

OTHER PUBLICATIONS

Lishner, M., et al., "Treatment of Diabetic Perforating Ulcers (Mal Perforant) with Local Dimethylsulfoxide," *J. Am Geriatr Soc.*, vol. 33, No. 1, pp. 41-43, (1985).

Lyubimova, N., et al., "Experimental Evidence to Support the Hypothesis that Damage to Vascular Endothelium Plays the Primary Role in the Development of Late Radiation-induced CNS Injury," *The British Journal of Radiology*, vol. 77, pp. 488-492, (2004).

Maehara, Y., *Fukuoka Medical Journal*, vol. 88, No. 11, 1997, pp. 337-344; No English Translation Available.

Magazu, S., et al., "α,α-Trehalose-Water Solutions. VIII. Study of the Diffusive Dynamics of Water by High-Resolution Quasi Elastic Neutron Scattering," *J. Phys. Chem. B*, vol. 110, No. 2, pp. 1020-1025, (2006).

Magesh, V., "Studies on the anti-tumor effect of crocetin against benzo(a)pyrene induced lung cancer in Swiss albino mice," Biomedicine, (Chennai india) (Dec. 31, 2003), vol. 23 (3rd & 4th Edition), pp. 96-99, Database HCAPLUS on STN, DN 141:388250, Abstract.

Marx, R.E., D.D.S., "Osteoradionecrosis: A New Concept of its Pathophysiology," *J. Oral Maxillofac Surg*, vol. 41, pp. 283-288, (1983).

Marx, R.E., et al., "Relationship of Oxygen Dose to Angiogenesis Induction in Irradiated Tissue," *The American Journal of Surgery*, vol. 160, pp. 519-524, (1990).

Mayer, R., et al., "Hyperbaric Oxygen and Radiotherapy," *Strahlenther. Onkol.*, vol. 181, No. 2, pp. 113-123, (2005); DOI: 10.1007/s00066-005-1277-y.

Miyagawa, H., et al., "Pathogenesis of Delayed Radiation Injury in the Rat Spinal Cord After X-ray Irradiation," *Neuropathology*, vol. 16, pp. 126-132, (1996).

Moelbert, S., et al., "Kosmotropes and Chaotropes: Modeling Preferential Exclusion, Binding and Aggregate Stability," *Biophysical Chemistry*, vol. 112, pp. 45-57, (2004); DOI: 10.1016/j.bpc.2004.06.012.

Notification Concerning Transmittal of International Preliminary Report on Patentability (Chapter 1 of the Patent Cooperation Treaty) for International Application No. PCT/US2008/012440 dated May 14, 2010.

Ohga, E., et al., "The relationship between adhesion molecules and hypoxia," Nippon Rinsho, vol. 58, No. 8, pp. 1587-1591, (2000); No English Translation Available.

Okeda, R., "Pathological Changes in the Cerebral Medullary Arteries of Five Autopsy Cases of Malignant Nephrosclerosis: Observation by Morphometry and Reconstruction of Serial Sections," *Neuropathology*, vol. 23, pp. 153-160, (2003).

Okonkwo, D.O., et al., "Trans-sodium Crocetinate Increases Oxygen Delivery to Brain Parenchyma in Rats on Oxygen Supplementation," *Neuroscience Letters*, vol. 352, pp. 97-100, (2003).

Pastores, S.M., et al., "Posttraumatic Multiple-organ Dysfunction Syndrome: Role of Mediators in Systemic Inflammation and Subsequent Organ Failure," *Academic Emergency Medicine*, vol. 3, No. 6, pp. 611-622, (1996).

Pauling, L., "Recent Work on the Configuration and Electronic Structure of Molecules; with some Applications to Natural Products," *Fortschr. Chem. Org. Naturst.*, vol. 3, No. 303, pp. 203-235, (1939).

Pfander, H., et al., "Carotenoid Synthesis: A Progress Report," *Pure & Appl. Chem.*, vol. 69, No. 10, pp. 2047-2060, (1997).

Pfitzner, I., et al., "Carotenoid: methyl-β-cyclodextrin formulations: an improved method for supplementation of cultured cells," *Biochimica et Biophysica Acta*, vol. 1474, No. 2, pp. 163-168, (2000), XP004276552.

Pharmacia, vol. 27, No. 7, pp. 703-705, (1991); No English Translation Available.

Polyakov, N.E., et al., "Inclusion Complexes of Carotenoids with Cyclodextrins: $^1$H NMR, EPR, and Optical Studies," *Free Radical Biology & Medicine*, vol. 36, No. 7, pp. 872-880, (2004); XP27231510.

Re, R., et al., "Isomerization of Lycopene in the Gastric Milieu," *Biochemical and Biophysical Research Communications*, vol. 281, No. 2, pp. 576-581, (2001); DOI: 10.1006/bbrc.2001.4366.

RN: 120523-11-7; CN: 2,4,6,8,10, 12,14,16,18-Eicosanonaenedioic acid, 4,8, 13,17-tetramethyl-potassium sodium salt, (1989).

RN: 147484-59-1; CN: 2,4,6,8-Decatetraenedioic acid, disodium salt, (1993).

RN: 33261-80-2; CN: 2,4,6,8,10,12,14,16,18-Eicosanonaenedioic acid, 4,8,13,17-tetramethyl-dipotassium salt, (1984).

RN: 33261-81-3; CN: 2,4,6,8,10,12,14,16,18-Eicosanonaenedioic acid, 4,8,13,17-tetramethyl-disodium salt, (1984).

Rowinsky, E. K., "Novel Radiation Sensitizers Targeting Tissue Hypoxia," *Oncology*, vol. 13, No. 10, Supplement No. 5, pp. 61-70, (1999), XP009044613.

Roy, J.W., et al, "A Novel Fluid Resuscitation Therapy for Hemorrhagic Shock," *Shock*, vol. 10, No. 3, pp. 213-217, (1998).

Schwieter, U., et al., "Synthesen in der Carotinoid-Reihe 20. Mitteilung[1]) Neue Synthesen von Apocarotinoiden," *Helvetica Chimica Acta*, vol. 49, pp. 369-390, (1966), XP-002575142.

Secor, R.M., "The Effect of Concentration on Diffusion Coefficient in Polymer Solutions," *A.I.Ch.E. Journal*, vol. 11, No. 3, pp. 452-456, (1965).

Seyde, W.C., et al., "Carotenoid Compound Crocetin Improves Cerebral Oxygenation in Hemorrhaged Rats," *Journal of Cerebral Blood Flow and Metabolism*, vol. 6, No. 6, pp. 703-707, (1986).

Shi, Nihon Butsuri Gakkai, "Structure and Function of Cartenoid in Photosynthetic System," *Journal of the Physical Society of Japan*, vol. 50, No. 7, pp. 555-561, (1995); No English Translation Available.

Singer, M., et al., "Intravenous Crocetinate Prolongs Survival in a Rat Model of Lethal Hypoxemia," *Crit Care Med*, vol. 28, No. 6, pp. 1968-1972, (2000).

Snyder, J.M., et al., "cis-trans Isomerization of Unsaturated Fatty Acids with p-Toluenesulfinic Acid," *J. Am. Oil Chem. Soc.*, vol. 59, No. 11, pp. 469-470, (1982).

Stennett, A.K., et al., "trans-Sodium Crocetinate and Diffusion Enhancement," *J. Phys. Chem. B.*, vol. 110, No. 37, pp. 18078-18080, (2006).

Streitwieser, A., et al., Introduction to Organic Chemistry, 2nd Ed., pp. 504-505, (1981).

The Lung perspectives, vol. 9, No. 2, pp. 161-165, (2001); No English Translation Available.

Tong, L., "Cyclodextrins Chemistry: Fundamentals and Application," *Science Press*, pp. 360-364, (2001); No English Translation Available.

Tyssandier, V., et al., "Processing of Vegetable-borne Carotenoids in the Human Stomach and Duodenum," *Am J Physiol Gastrointest Liver Physiol*, vol. 284: G913-G923, (2003).

Vickackaite, V., et al., "Photochemical and Thermal Degradation of a Naturally Occuring Dye Used in Artistic Painting. A Chromatographic, Spectrophotometric and Fluorimetric Study on Saffron," *International Journal of Photoenergy*, vol. 6, pp. 175-183, (2004).

Wang, Y., et al., "The Effect of Trans-Sodium Crocetinate in a Model of Intracranial Hemorrhage," Abstracts of the Annual Meeting of the Society for Neuroscience, Society for Neuroscience Abstract Viewer and Itinerary Planner, 2 pages, (Nov. 15, 2008) Washington, DC, XP009163975.

Wenkert, E., et al., "Polyene Synthesis. Ready Construction of Retinol-Carotene Fragments (±)-6-(E)-LTB, Leukotrienes, and Corticrocin," *Journal of Organic Chemistry*, vol. 55, No. 25, pp. 6203-6214, (1990), XP002317164.

White, D.C., "The Histopathologic Basis for Functional Decrements in Late Radiation Injury in Diverse Organs," *Cancer*, vol. 37, No. 2, pp. 1126-1143, February Supplement, (1976).

Widmer, E., et al., "Technical Procedures for the Syntheses of Carotenoids and Related Compounds from 6-Oxo-isophorone: Syntheses of (3R.3R)-Zeaxanthin," *Helvetica Chemica Acta*, vol. 73, pp. 861-867, (1990).

Wilkins, E.S., et al., "The Effect of Crocetin on the Irradiation of Walker-256: In Vitro and In Vivo Studies," *Cancer Biochem. Biophys.*, vol. 3, pp. 71-74, (1979), XP008157982.

Williamson, R.A., "An Experimental Study of the Use of Hyperbaric Oxygen to Reduce the Side Effects of Radiation Treatment for Malignant Disease," *Int. J. Oral Maxillofac. Surg.*, vol. 36, pp. 533-540, (2007).

(56) References Cited

OTHER PUBLICATIONS

Wirz, R., et al., "Celluloseaffinität von Polyendicarbonsäuren vom Typ des Crocetins und von quarternären Ammoniumverbindungen," *Helv. Chim. Acta*, vol. 63, No. 6, pp. 1738-1745, (1960), XP008042762.
Wurtman, R.J., "Alzheimer's Disease," *Scientific American*, vol. 252, (1985).
Yamaguchi, K., et al., "Kinetics of $O_2$ Uptake and Release by Human Erythrocytes Studied by a Stopped-flow Technique," *The American Physiological Society*, vol. 58, pp. 1215-1224, (1985).
Zheng, S., et al., "Crocetin Attenuates Atherosclerosis in Hyperlipidemic Rabbits Through Inhibition of LDL Oxidation," *J. Cardiovasc. Pharmacol*, vol. 47, No. 1, pp. 70-76, (2006); XP009135396, ISSN: 0160-2446.
Search Report dated Sep. 15, 2015, issued in Chinese Patent Application No. 201080027664.7 and English translation.
Search Report dated Dec. 14, 2015, issued in Chinese Application No. 201180033875.6, which corresponds to PCT/US2011/000997, and English translation.
Search Report dated Oct. 21, 2016, issued in Chinese Application No. 201510128602.X, which is a national phase of PCT/US2006/006422, and English translation.
Supplementary Partial European Search Report in Feb. 25, 2005 based on Application No. EP 03 71 1221.
Supplementary Partial European Search Report dated Apr. 21, 2005 based on Application No. EP 03 71 1221.
Supplementary Partial European Search Report dated Nov. 7, 2006.
Supplementary European Search Report dated Apr. 29, 2010 issued by the European Patent Office in one of Applicants' corresponding foreign applications.
Supplementary European Search Report dated Dec. 8, 2010 (corresponding to applicant's European Regional Phase Patent Application No. EP 08844993.9 based on International Patent Application No. PCT/US2008/012440 filed on Oct. 31, 2008).
Supplementary European Search Report dated Oct. 29, 2012 issued by the European Patent Office and Preliminary Opinion.
Supplementary Extended European Search Report dated Nov. 21, 2012 issued by the European Patent Office and Preliminary Opinion.
Supplementary (Extended) European Search Report dated Oct. 21, 2013 in European Patent Application No. EP 11790107.4 issued from PCT/US2011/000997 filed on Jun. 2, 2011, together with the Written Opinion.
Supplementary Extended European Search Report dated Mar. 28, 2013 issued by the European Patent Office and Written Opinion.
Australian Office Action dated Jun. 25, 2008 from corresponding Australian Patent Office.
Australian Office Action dated Mar. 26, 2010 in Applicant's Australian Application No. 2003265617.
Australian Office Action dated Oct. 25, 2010 issued by the Australian Patent Office in one of Applicants' corresponding foreign applications.
Australian Office Action dated Dec. 23, 2011.
Australian Office Action dated Dec. 3, 2014 from the Australian Patent Office for applicant's Australian application corresponding to PCT Application No. PCT/US03/26424.
Australian Office Action dated Dec. 10, 2014 from applicant's Australian application corresponding to PCT Application No. PCT/US2008/012440.
Australian Office Action dated Feb. 25, 2015 from applicant's application corresponding to PCT Application No. PCT/US2011/000997.
Australian Examination Report No. 1 dated Dec. 1, 2016, issued in Australian Patent Application No. 2016201192, which is a National Phase of PCT/US2011/000997.
Canadian Office Action dated Mar. 26, 2013, for applicant's Canadian Patent Application No. 2,598,882 corresponding to PCT/US06/006422 filed Feb. 24, 2006.
Canadian Office Action dated May 30, 2013, for applicant's Canadian Patent Application No. 2,683,760 corresponding to PCT/US2008/004708 filed Apr. 11, 2008.
Canadian Office Action dated Oct. 20, 2009 from Canadian Application No. 2,477,245.
Canadian Office Action dated Jul. 7, 2010 in corresponding Canadian Application No. 2,477,245.
Canadian Office Action dated Oct. 26, 2010 in corresponding Canadian Application No. 2,537,210.
Canadian Office Action dated Jul. 5, 2011 in corresponding Canadian Application No. 2,537,210.
Canadian Office Action dated Nov. 4, 2014 in Canadian Patent Application No. 2,703,946 from national phase of PCT/US2008/012440.
Canadian Office Action dated Apr. 12, 2016, issued in Canadian Patent Application No. 2,765,697, which is the national phase of PCT/US2010/001794.
Canadian Office Action dated Aug. 3, 2016, issued in Canadian Patent Application No. 2,703,946, which corresponds to PCT/US2008/012440.
Canadian Office Action dated Aug. 31, 2016, issued in Canadian Patent Application No. 2,598,882, which is the national phase of PCT/US2006/06422.
Chinese Office Action dated Nov. 7, 2008 in a corresponding application owned by the applicants in Chinese Application No. 03826969.4.
Chinese Third Office Action in Chinese Patent Application No. 03804566.4 dated Jan. 23, 2009 (English Translation Only).
Chinese Office Action and its English Translation dated Feb. 12, 2010 in the Assignee's Chinese application relating to PCT/US2006/006422.
Chinese Office Action dated Mar. 29, 2010 from Chinese Patent Application No. 03826969.4 based on PCT/US2003/026424.
Chinese Office Action and its English Translation dated Feb. 21, 2011 in Assignee's Chinese Patent Application No. 200680013663.0 based on PCT/US2006/006422.
Chinese Office Action and its English Translation dated Apr. 6, 2011 from Chinese Patent Application No. 200680013663.0 based on PCT/US2006/006422.
Chinese Office Action and its English Translation dated Jun. 30, 2011 in Chinese Application No. 2008801143109 (English Translation Only).
Chinese Office Action and its English Translation dated Jan. 18, 2012 in Chinese Patent Application No. 200680013663.0 based on PCT/US2006/006422.
Chinese Office Action and its English translation dated May 3, 2012, from Chinese Patent Application No. 03804566.4 based on PCT/US2003/005521.
Chinese Office Action and its English translation dated Jun. 6, 2012, from Chinese Patent Application No. 200880015671.8 based on PCT/US2008/004708.
Chinese Office Action and its English Translation dated Jun. 14, 2012 from Chinese Patent Application No. 200880114310.9 that corresponds to PCT/US2008/012440.
Chinese Office Action and its English Translation dated Jan. 28, 2013, from Chinese Patent Application No. 200880015671.8 that corresponds to PCT/US2008/004708.
Chinese Patent Office Decision of Rejection dated May 2, 2013 and its English translation, corresponding to PCT/US2006/06422 filed on Feb. 24, 2006.
Chinese Office Action dated May 6, 2013, from Chinese Patent Application No. 201080027664.7 that corresponds to PCT/US2010/001794, and its English translation.
Chinese Office Action dated Jul. 9, 2013, from Chinese Patent Application No. 200880114310.9 that corresponds to PCT/US2008/012440, and its English translation.
Chinese Office Action and its English translation dated Nov. 1, 2013, from Chinese Patent Application No. 201180033875.6 that corresponds to PCT/US2011/000997.
Chinese Office Action and its English translation dated Mar. 19, 2014, from Chinese Patent Application No. 200880015671.8 that corresponds to PCT/US2008/004708.
Chinese Office Action and its English translation dated Mar. 31, 2014, from Chinese Patent Application No. 201210063676.6 that corresponds to PCT/US2003/026424, filed Aug. 25, 2003.

(56) References Cited

OTHER PUBLICATIONS

Chinese Office Action and English Translation dated Jul. 21, 2014 issued in Chinese Patent Application No. 200680013663.0, 9 pp.
Chinese Office Action and English Translation dated Jul. 24, 2014 issued in Chinese Patent Application No. 200880114310.9, 19 pp.
Chinese Office Action dated Aug. 15, 2014 issued in Chinese Patent Application No. 201080027664.7 and English Translation, 13 pp.
Chinese Office Action and English Translation dated Dec. 8, 2014 (Reexamination Decision) from the Chinese Patent Office in applicant's Chinese Application corresponding to PCT Application No. PCT/US06/06422.
Chinese Notice and Office Action and English Translations dated Dec. 22, 2014 from the China Patent Office for applicant's China application corresponding to PCT Application No. PCT/US2011/000997.
Chinese Office Action and its English translation dated May 5, 2015 for national phase of PCT/US2008/004708.
Chinese Office Action and its English translation dated Jun. 24, 2015 for National Phase of PCT/US03/26424 (with translation).
Chinese Fifth Notification of Office Action dated Aug. 17, 2015, issued in Chinese Patent Application No. 200880114310.9 and English translation.
Chinese Third Notification of Office Action dated Sep. 25, 2015, issued in Chinese Patent Application No. 201080027664.7 and English translation.
Chinese Third Notification of Office Action dated Dec. 14, 2015, issued in Chinese Application No. 201180033875.6, which corresponds to PCT/US2011/000997, and English translation.
Chinese Fifth Notification of Office Action dated Jun. 21, 2016, issued in Chinese Patent Application No. 200880015671.8, which is the national phase of PCT/US2008/04708, and English translation.
Chinese Sixth Notification of Office Action dated Aug. 16, 2016, issued in Chinese Patent Application No. 200880114310.9, which is the national phase of PCT/US2008/012440, and English translation.
Chinese First Notification of Office Action dated Oct. 31, 2016, issued in Chinese Application No. 201510128602.X, which is a National Phase of PCT/US2006/006422, and English translation.
Chinese Decision of Rejection dated Nov. 10, 2016, issued in Chinese Application No. 201080027664.7, which is a National Phase of PCT/US2010/001794, and English translation.
Chinese Decision for Rejection and its English Translation dated Nov. 28, 2016 issued in Chinese Patent Application No. 201180033875.6 which is a national phase of PCT/US2011/000997.
Chinese Search Report dated Mar. 18, 2013, and its English translation.
Chinese Search Report dated Jun. 27, 2013, and its English translation.
Chinese Search Report and its English translation dated Mar. 19, 2014, from Chinese Patent Application No. 201210063676.6 that corresponds to PCT/US2003/026424, filed Aug. 25, 2003.
Chinese Search Report dated Oct. 21, 2016, issued in Chinese Application No. 201510128602.X, which is a national phase of PCT/US06/06422, and English translation.
Eurasian Patent Office Action and its English translation dated Nov. 9, 2011.
Eurasian Patent Office Action and its English translation dated Nov. 17, 2011.
European Office Action dated Nov. 9, 2009 in Applicant's European application corresponding to PCT/US2003/005521.
European Office Action dated Nov. 9, 2009 in Applicant's European application corresponding to PCT/US2003/026424.
European Office Action dated Apr. 7, 2011, from European Patent Application No. EP 08742781.1.
European Office Action dated Oct. 17, 2011 from European Patent Application No. EP 08742781.1.
European Office Action dated Oct. 31, 2011, from European Patent Application No. EP 06758166.0.
European Office Action dated Apr. 25, 2012.
European Office Action dated Jun. 11, 2012, from European Patent Application No. EP 08742781.1.
European Office Action dated Mar. 12, 2014, from applicant's European Patent Application No. EP 12166293.6, corresponding to PCT/US2006/006422 filed Feb. 24, 2006.
European Office Action dated Nov. 21, 2014 from the EPO for applicant's EP Application No. 03818748.0 based on PCT/US2003/26424.
European Office Action dated Feb. 2, 2015 from the for applicant's application corresponding to PCT Application No. PCT/US2008/012440.
European Office Action dated Feb. 2, 2015 from the for applicant's application corresponding to PCT Application No. PCT/US03/05521.
European Office Action dated Oct. 27, 2015 that issued in the European application that corresponds to PCT//US03/05521.
European Communication pursuant to Article 94(3) EPC dated May 17, 2016, issued in European Patent Application No. 03 711 221.6, which is the national phase of PCT/US03/05521.
European Communication pursuant to Article 94(3) EPC dated May 19, 2016, issued in European Patent Application No. 03 818 748.0, which is the national phase of PCT/US03/26424.
European Communication pursuant to Article 94(3) EPC dated Jun. 3, 2016, issued in European Patent Application No. 11 790 107.4, which is the national phase of PCT/US2011/000997.
European Communication Pursuant to Article 94(3) EPC dated Jul. 6, 2016, issued in European Patent Application No. 12 166 293.6, which is the national phase of PCT/US2006/006422.
Hungarian Novelty Search Report dated Nov. 5, 2009 (w/translation).
India Office Action dated Oct. 23, 2008 in a corresponding application owned by the applicants (India Patent App No. 676/DELNP/2006).
India Examination Report dated Apr. 12, 2010 issued by the India Patent Office in one of Applicants' corresponding foreign applications.
India Office Action (Examination Report) dated Feb. 21, 2013, for applicant's India Patent Application No. 6688/DELNP/2007 corresponding to PCT/US2006/006422 filed Feb. 24, 2006.
India Office Action dated Dec. 31, 2014 from the India Patent Office for applicant's India application corresponding to PCT Application No. PCT/US2008/04708.
India Office Action dated Jul. 21, 2015 for National Phase of PCT/US2003/26424.
India Office Action dated Jul. 23, 2015 for National Phase of PCT/US2008/012440.
India Office Action dated Aug. 23, 2016, issued in Indian Patent Application No. 6834/DELNP/2009, which is the national phase of PCT/US2008/04708.
Israeli Office Action dated Apr. 10, 2013, from applicant's Israel Patent Application No. 185460 corresponding to PCT/US06/06422 filed Feb. 24, 2006, and its English translation.
Israeli Office Action dated Oct. 29, 2013, from Israel Patent Application No. 201438 that corresponds to PCT/US2008/004708, and its English translation.
Israeli Office Action and English Translation dated May 4, 2014 from applicant's Israel Patent Application No. 185460 corresponding to PCT/US06/06422 filed Feb. 24, 2006.
Israeli Office Action dated Feb. 1, 2015 for applicant's application corresponding to PCT Application No. PCT/US2003/026424.
Israeli Office Action dated Dec. 30, 2015, issued in Israeli Patent Application No. 216919, which corresponds to PCT/US2010/001794, and English translation.
Japanese Patent Office Action dated Jun. 2, 2009 and its English translation, cited in one of Assignee's Japanese Patent Application No. 2003-571422.
Japanese Patent Office Action dated Jun. 9, 2009 and its English translation, cited in one of Assignee's Japanese patent applications.
Japanese Decision of Rejection dated Jan. 12, 2010 and its English translation, corresponding to PCT/US2003/005521 corresponding to Diffusion's U.S. Pat. No. 7,351,844.
Japanese Office Action and its English Translation dated Jan. 12, 2010 in the Assignee's Japanese application relating to PCT/US2003/026424.

(56) References Cited

OTHER PUBLICATIONS

Japanese Office Action and its English Translation dated Apr. 6, 2010 in the Assignee's Japanese application relating to PCT/US2006/006422.
Japanese Notice of Reasons for Rejection and its English Translation dated May 24, 2011 issued in Japanese Patent Appln. No. 2007-557157 (corresponding to PCT/US2006/006422).
Japanese Office Action and its English Translation dated Oct. 4, 2011.
Japanese Office Action and its English Translation dated Jul. 10, 2012 for Applicant's Japanese Patent Application No. 2009-274988 corresponding to PCT/US2003/005521, filed Feb. 25, 2003.
Japanese Office Action and its English Translation dated Jul. 10, 2012 from Japanese Application No. 2009-279890 based on PCT/US2003/026424.
Japanese Office Action (Notice of Reasons for Rejection) dated Jan. 29, 2013, for applicant's Japanese Patent Application No. 2010-503069 corresponding to PCT/US08/004708 filed Apr. 11, 2008, and its English translation.
Japanese Patent Office Action dated Feb. 19, 2013, from applicant's Japanese Patent Application No. 2009-279890 corresponding to PCT/US03/26424 filed Aug. 25, 2003, and its English translation.
Japanese Decision of Rejection dated May 21, 2013, from applicant's Japanese Patent Application No. 2010-110185 corresponding to PCT/US2003/05521 filed Feb. 25,2003, and its English translation.
Japanese Office Action (Notice of Reasons for Rejection) and its English translation dated Jun. 4, 2013, from applicant's Japanese Patent Application No. 2011-209754 corresponding to PCT/US06/06422 filed Feb. 24, 2006.
Japanese Office Action (Reasons for Rejection) dated Jun. 18, 2013, in Japanese App. No. 2010-531078 (no English translation).
Japanese Office Action (Final Rejection) and its English translation dated Sep. 10, 2013, from applicant's Japanese Application No. P2009-279890 corresponding to PCT/US03/26424 filed Aug. 25, 2003.
Japanese Office Action (Final Rejection) and its English translation dated Nov. 26, 2013, from applicant's Japanese Application No. P2010-503069 corresponding to PCT/US08/004708 filed Apr. 11, 2008.
Japanese Office Action (Final Rejection) and its English translation dated Feb. 4, 2014 from applicant's Japanese Application No. P2011-209754 corresponding to PCT/US06/06422 filed Feb. 24, 2006.
Japanese Office Action and its English translation dated Apr. 22, 2014 from applicant's Japanese Application No. P2010-531078 corresponding to PCT/US08/012440 filed Oct. 31, 2008.
Japanese Office Action dated Jun. 24, 2014 issued in Japanese Patent Application No. P2012-516071 and English Translation, 10 pp.
Japanese Office Action and its English translation dated Sep. 9, 2014 issued in Japanese Patent Application No. P2010-531078, 6 pp.
Japanese Office Action and English Translation dated Sep. 9, 2014 issued in Japanese Patent Application No. 2013-197629, 6 pp.
Japanese Office Action and English translation dated Sep. 24, 2014 issued in Japanese Patent Application No. P2011-209754, 5 pp.
Japanese Office Action dated Jan. 27, 2015 from the for applicant's application corresponding to PCT Application No. PCT/US03/26424.
Japanese Office Action and its English translation dated Apr. 14, 2015 for national phase of PCT/US2008/012440.
Japanese Office Action and its English translation dated Apr. 21, 2015 for national phase of PCT/US2008/04708.
Japanese Office Action and its English translation dated Apr. 21, 2015 for national phase of PCT/US2011/000997.
Japanese Official Action dated Sep. 8, 2015.
Japanese Final Rejection dated Nov. 24, 2015, issued in Japanese Patent Application No. P2013-513151, which corresponds to PCT/US2011/000997, and English translation.
Japanese Notice of Reasons for Rejection dated Nov. 24, 2015, issued in Japanese Patent Application No. P2015-011575, which corresponds to PCT/US2006/006422, and English translation.
Japanese Office Action dated Jan. 12, 2016, issued in Japanese Patent Application No. 2014-003614, which corresponds to PCT/US2003/026424.
Japanese Final Rejection dated Mar. 1, 2016, issued in Japanese Patent Application No. P2014-061897, which corresponds to PCT/US2008/004708, and English translation.
Japanese Notice of Reasons for Rejection dated Jun. 21, 2016, issued in Japanese Patent Application No. 2015-159872 and English translation.
Japanese Final Rejection dated Jun. 28, 2016, issued in Japanese Patent Application No. 2015-011575, which is the national phase of PCT/US2006/006422, and English translation.
Korean Office Action dated May 26, 2009, and English translation in a corresponding application owned by the applicants.
Korean Office Action dated Nov. 23, 2009 in applicant's corresponding Korean application No. 10-2006-7003827.
Korean Office Action and its English Translation dated Jun. 22, 2010 from Applicant's Korean Patent Appln. No. 10-2006-7003827, that corresponds to PCT/US2003/026424.
Korean Office Action and its English Translation dated Jul. 6, 2010 in the Assignee's Korean Application No. 10-2004-17013118, that is the Nationalized Appln. from PCT/US03/005521, claiming priority from U.S. Appl. No. 60/358,718.
Korean Patent Office Action dated Sep. 26, 2012, from Korean Patent Application No. 10-2007-7021197 based on PCT/US2006/006422, and its English translation.
Korean Office Action and English Translation dated Jul. 28, 2014 issued in Korean Patent Application No. 10-2009-7023432, 8 pp.
Korean Office Action dated Jan. 16, 2015 from the South Korea Patent Office for applicant's application corresponding to PCT Application No. PCT/US2008/012440.
Korean Office Action dated May 27, 2015 and its English translation for Application No. 10-2009-7023432 (national phase of PCT/US2008/04708).
Korean Notice of Preliminary Rejection dated Nov. 24, 2015, issued in Korean Application No. 10-2010-7010445, which corresponds to PCT/US2008/012440, and English translation.
Korean Notice of Preliminary Rejection dated Jul. 26, 2016, issued in South Korean Patent Application No. 10-2012-7001265, which is the national phase of PCT/US2010/001794, and English translation.
Mexican Office Action dated Feb. 23, 2009 in a corresponding application owned by the applicants in Mexican Patent Appln. No. PA/a/2004/008253.
Mexican Office Action dated May 2010, and its English translation of rejected parts of the Office Action, from Mexican Patent Application No. PA/a/2004/008253 corresponding to International Patent Application No. PCT/EP2003/005521.
Mexican Office Action and its English translation dated Oct. 20, 2011.
Mexican Office Action dated Aug. 27, 2012, corresponding to U.S. Appl. No. 12/081,236, filed Apr. 11, 2008 (No English Translation Available).
New Zealand Examination Report dated Jan. 8, 2008 from corresponding New Zealand Patent Office.
New Zealand Examination Report dated Oct. 6, 2008 issued by the New Zealand Patent Office in one of Applicants' corresponding foreign applications.
New Zealand Examination Report dated Jul. 2, 2009 issued by the New Zealand Patent Office in one of Applicants' corresponding foreign applications.
New Zealand Examination Report dated Apr. 7, 2010 issued by the New Zealand Patent Office in Applicants' corresponding foreign Application No. 584433.
New Zealand Examination Report dated Oct. 7, 2010 issued by the New Zealand Patent Office in one of Applicants' corresponding foreign applications.
New Zealand Examination Report dated Jan. 21, 2011.
New Zealand Examination Report dated Oct. 2011 issued by the New Zealand Patent Office in Applicants' corresponding foreign Application No. 595624.

(56) References Cited

OTHER PUBLICATIONS

Norwegian Office Action and its English Translation dated Jun. 22, 2010 in the Assignee's Norwegian application relating to PCT/US2003/005521.
Norwegian Office Action and its English Translation dated Feb. 16, 2011, from Norway Patent Application No. 20043661, based on International Patent Application No. PCT/US2008/012440.
Polish Office Action dated Feb. 23, 2010 from Polish Patent Application No. P-373780 based on PCT/US2003/005521.
Polish Office Action dated Sep. 2010 in corresponding Polish Application No. P-373780.
Ukraine Office Action dated Aug. 2010.
U.S. Final Office Action dated Dec. 4, 2008 from U.S. Appl. No. 11/361,054, 6 pages.
U.S. Non-Final Office Action dated Aug. 24, 2007, in U.S. Appl. No. 11/790,779, 6 pages.
U.S. Non-Final Office Action dated Sep. 28, 2007, in U.S. Appl. No. 11/723,383, 5 pages.
U.S. Non-Final Office Action dated Nov. 13, 2008, in U.S. Appl. No. 10/647,132, 7 pages.
U.S. Non-Final Office Action dated Oct. 28, 2009, in U.S. Appl. No. 11/361,054, 5 pages.
U.S. Non-Final Office Action dated Sep. 22, 2011, in U.S. Appl. No. 11/790,779, 8 pages.
U.S. Non-Final Office Action dated Dec. 19, 2011 in U.S. Appl. No. 12/801,726, 7 pages.
U.S. Non-Final Office Action dated Jan. 4, 2012 in U.S. Appl. No. 13/137,337, 5 pages.
U.S. Non-Final Office Action dated Jan. 24, 2012 in U.S. Appl. No. 13/137,322, 9 pages.
U.S. Non-Final Office Action dated Mar. 16, 2012 in U.S. Appl. No. 13/137,324, 5 pages.
U.S. Non-Final Office Action dated May 10, 2012 in U.S. Appl. No. 13/067,469, 17 pages.
U.S. Final Office Action dated Jul. 26, 2012 in U.S. Appl. No. 12/801,726, 6 pages.
U.S. Non-Final Office Action dated Sep. 6, 2012 in U.S. Appl. No. 13/137,322, 9 pages.
U.S. Final Office Action dated Sep. 18, 2012 in U.S. Appl. No. 13/137,337, 5 pages.
U.S. Final Office Action dated Dec. 24, 2012 in U.S. Appl. No. 13/137,324, 10 pages.
U.S. Final Office Action dated Jan. 15, 2013 from U.S. Appl. No. 13/067,469, 21 pages.
U.S. Final Office Action dated Apr. 5, 2013 from U.S. Appl. No. 13/137,322, 10 pages.
U.S. Final Office Action dated Jun. 12, 2013 from U.S. Appl. No. 12/801,726, 6 pages.
U.S. Advisory Office Action dated Jul. 16, 2013 in U.S. Appl. No. 13/137,324, 7 pages.
U.S. Non-Final Office Action dated Jul. 29, 2013 from U.S. Appl. No. 13/067,469, 21 pages.
U.S. Non-Final Office Action dated Aug. 22, 2013 from U.S. Appl. No. 13/507,365, 6 pages.
U.S. Final Office Action dated Nov. 20, 2013 in U.S. Appl. No. 13/137,337, 5 pages.
U.S. Non-Final Office Action dated Dec. 6, 2013 from U.S. Appl. No. 13/137,322, 8 pages.
U.S. Non-Final Office Action dated Jan. 30, 2014 from U.S. Appl. No. 12/801,726, 5 pages.
U.S. Final Office Action dated May 8, 2014 from U.S. Appl. No. 13/507,365, 5 pages.
U.S. Non-Final Office Action dated Jun. 5, 2014 from U.S. Appl. No. 13/067,469, 26 pages, Gainer.
U.S. Non-Final Office Action dated Jun. 9, 2014 from U.S. Appl. No. 13/137,324, 7 pages, Gainer et al.
U.S. Non-Final Office Action dated Jun. 26, 2014 in U.S. Appl. No. 13/137,337, 5 pages.
U.S. Final Office Action dated Sep. 8, 2014 issued in U.S. Appl. No. 12/801,726, 23 pages.
U.S. Non-Final Office Action dated Oct. 1, 2014 issued in U.S. Appl. No. 13/621,650, 51 pages.
U.S. Final Office Action dated Nov. 25, 2014 in U.S. Appl. No. 13/067,469, 13 pages.
U.S. Non-Final Office Action dated Dec. 8, 2014 in U.S. Appl. No. 13/137,324, 11 pages.
U.S. Non-Final Office Action dated Dec. 29, 2014 in U.S. Appl. No. 13/507,365, 5 pages.
U.S. Non-Final Office Action dated Apr. 29, 2015, in U.S. Appl. No. 12/801,726, 6 pages.
U.S. Final Office Action dated Jun. 4, 2015 for U.S. Appl. No. 13/621,650, 6 pages.
U.S. Final Office Action dated Jul. 9, 2015 for U.S. Appl. No. 13/137,324, 6 pages.
U.S. Final Office Action dated Aug. 13, 2015 for U.S. Appl. No. 13/507,365, 5 pages.
U.S. Non-Final Office Action dated Sep. 30, 2015 in U.S. Appl. No. 13/137,337, 4 pages.
U.S. Final Office Action dated Nov. 12, 2015 for U.S. Appl. No. 12/801,726, 6 pages.
U.S. Non-Final Office Action dated Mar. 16, 2016 for U.S. Appl. No. 13/507,365, 4 pages.
U.S. Non-Final Office Action dated May 5, 2016, issued in U.S. Appl. No. 12/801,726, which corresponds to PCT/US2010/001794, 6 pages.
U.S. Non-Final Office Action dated Oct. 12, 2016, issued in U.S. Appl. No. 14/642,703, which corresponds to PCT/US2011/000997, 15 pages.
U.S. Final Office Action dated Nov. 14, 2016, issued in U.S. Appl. No. 12/801,726, which corresponds to PCT/US2010/001794, 11 pages.
Bazan, N., et al., "Hypoxia Signaling to Genes," Molecular Neurobiology, vol. 26, Nos. 2-3, pp. 283-298, (2002).
Buchta, E. et al., "Eine Totalsynthese des „all"-trans-2,2'-Desdimethyl-crocetin-dimethyl-esters und des „all"-trans-Crocetin-dimethylesters," Naturwissenschaften, (1959).
Buchta, E. et al., "Eine Totalsynthese des „all"-trans-Crocetin-dimethylesters," Chemischte Berichte, vol. 93, pp. 1349-1353, (1960).
International Search Report for International Application No. PCT/IB2002/004923, Date of publication of the international search report dated Dec. 23, 2004, 8 pages.
Mohler III, E.R., et al., "Evaluation of Trans Sodium Crocetinate on Safety and Exercise Performance in Patients with Peripheral Artery Disease and Intermittent Claudication," NIH Public Access, Author Manuscript, doi: 10.1177/1358863X11422742, 14 pages, First page of document states: Published in final edited form as: *Vasc. Med.* Oct. 2011; 16(5): 346-353.
Clinical Trials.gov, "Trans Sodium Crocetinate (TSC) Study of Intra-tumoral Oxygen Concentration, Safety, and Pharmacokinetics in Patients With High Grade Glioma," ClinicalTrials.gov Identifier: NCT00826930, 7 pages, retrieved on Nov. 27, 2019, from: https://clinicaltrials.gov/ct2/show/NCT00826930.
ClinicalTrials.gov, "Safety and Efficacy of Trans Sodium Crocetinate (TSC) With Radiation and Temozolomide in Newly Diagnosed Glioblastoma," ClinicalTrials.gov Identifier: NCT01465347, 9 pages, retrieved on Nov. 27, 2019, from: https://clinicaltrials.gov/ct2/show/NCT01465347.
Gainer, J.L. et al, "Trans Sodium Crocetinate with Temozolomide and Radiation Therapy for Glioblastoma Multiforme," J Neurosurg, vol. 126, pp. 460-466, (2017), Published online May 13, 2016; doi: 10.3171/2016.3.JNS152693.
Ibanez, B. et al., "2017 ESC Guidelines for the Management of Acute Myocardial Infarction in Patients Presenting with ST-Segment Elevation: The Task Force for the Management of Acute Myocardial Infarction in Patients Presenting with ST-Segment Elevation of the European Society of Cardiology," European Heart Journal, vol. 39, pp. 119-177, (2018).
"Managing Acute Ischemic Stroke: IV TPA," American Academy of Neurology, 2 pages, dated 2013, retrieved on Nov. 27, 2019, from: https://www.aan.com/Guidelines/Home/GetGuidelineContent/585.
Murray, R., "Pharmacokinetics of TSC and the Treatment of Hypoxic States," A Dissertation Presented to the Faculty of the School of

(56) References Cited

OTHER PUBLICATIONS

Engineering and Applied Science, University of Virginia, 106 pages, retrieved on Sep. 5, 2019, from: https://media.proquest.com/media/pq/classic/doc/888859001/fmt/ai/rep/SPDF?_s=eOSFva3r5jHJaP4%2FUSCxt3i9uLU%3D.
O'Gara, P. et al., "2013 ACCF/AHA Guideline for the Management of ST-Elevation Myocardial Infarction: A Report of the American College of Cardiology Foundation/American Heart Association Task Force on Practice Guidelines," Circulation, vol. 127, pp. e362-e425, (2013).
Powers, W. et al., "2018 Guidelines for the Early Management of Patients with Acute Ischemic Stroke: A Guideline for Healthcare Professionals from the American Heart Association/American Stroke Association," Stroke, vol. 49, pp. e46-e99, (2018).
Stennett, A. et al., "Trans-Sodium Crocetinate and Hemorrhagic Shock," Shock, vol. 28, No. 3, pp. 339-344, (2007).
Stennett, A., "Mechanism of Action of TSC," A Dissertation Presented to the Faculty of the School of Engineering and Applied Science, University of Virginia, 191 pages, retrieved on Sep. 5, 2019, from: https://media.proquest.com/media/pq/classic/doc/888858991/fmt/ai/rep/SPDF?_s=RXVfuP3SH6vxf1TE4SVMciZ8bfc%3D.
Wang, Y. et al., "Trans-Sodium Crocetinate Improves Outcomes in Rodent Models of Occlusive and Hemorrhagic Stroke," NIH Public Access, Author Manuscript, available in PMC 2015, 18 pages, face of article states: *Brain Res*. Oct. 2, 2014; 1583: 245-254, doi: 10.1016/j.brainres.2014.08.013.
Cheng, N.T. et al., "Intravenous Thrombolysis for Acute Ischemic Stroke Within 3 Hours Versus Between 3 and 4.5 Hours of Symptom Onset," The Neurohospitalist, vol. 5, Issue 3, pp. 101-109, (2015).
Ghandehari, K. et al., "Thrombolysis in Stroke Patients; Problems and Limitations," Iran J Med Sci, vol. 35, Issue 2, pp. 145-148, (2010).
Hepple, R. et al., "No Effect of Trans Sodium Crocetinate on Maximal $O_2$ Conductance or $V_{O2,max}$ in Moderate Hypoxia," Respiratory Physiology & Neurobiology, vol. 134, pp. 239-246, (2003).
Manabe, H. et al., "Metabolic Reflow as a Therapy for Ischemic Brain Injury," Acta Neurochirurgica Supplementum, vol. 110/2, pp. 87-91, (2011).
Manabe, H. et al., "Protection Against Focal Ischemic Injury to the Brain by Trans-Sodium Crocetinate: Laboratory Investigation," NIH Public Access, Author Manuscript, available in PMC 2012, 18 pages, doi: 10.3171/2009.10.JNS09562, face of article states: Published in final edited form as: *J Neurosurg*. Oct. 2010; 113(4): 802-809.
Wagner, P. et al., "Effects of Crocetin on Pulmonary Gas Exchange in Foxhounds During Hypoxic Exercise," J Appl Physiol, vol. 89, pp. 235-241, (2000).
Wang, Y. et al., "Perihematomal Cellular Injury Is Reduced by Trans-Sodium Crocetinate in a Model of Intracerebral Hemorrhage," Mol Neurobiol, vol. 52, pp. 985-989, (2015).

* cited by examiner

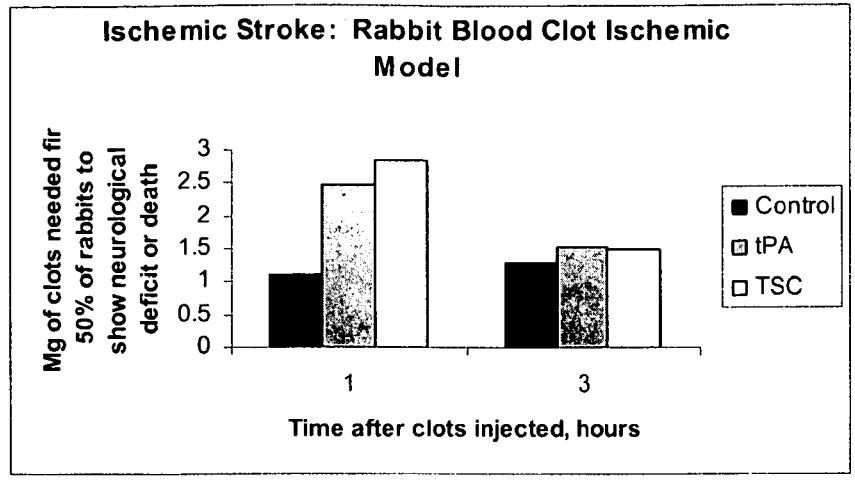
Figure 3: Single Drug Treatment
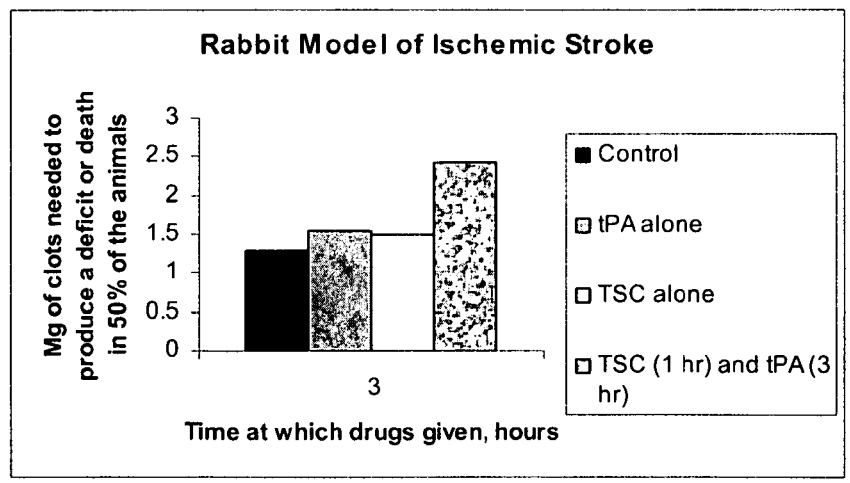
Figure 4: Combination Therapy Versus Single Drug Therapy

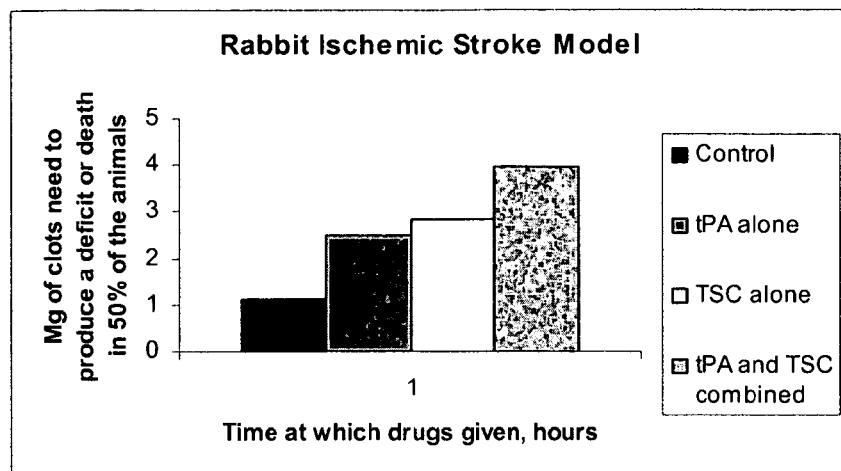
Figure 5: Various Treatments at 1 hour
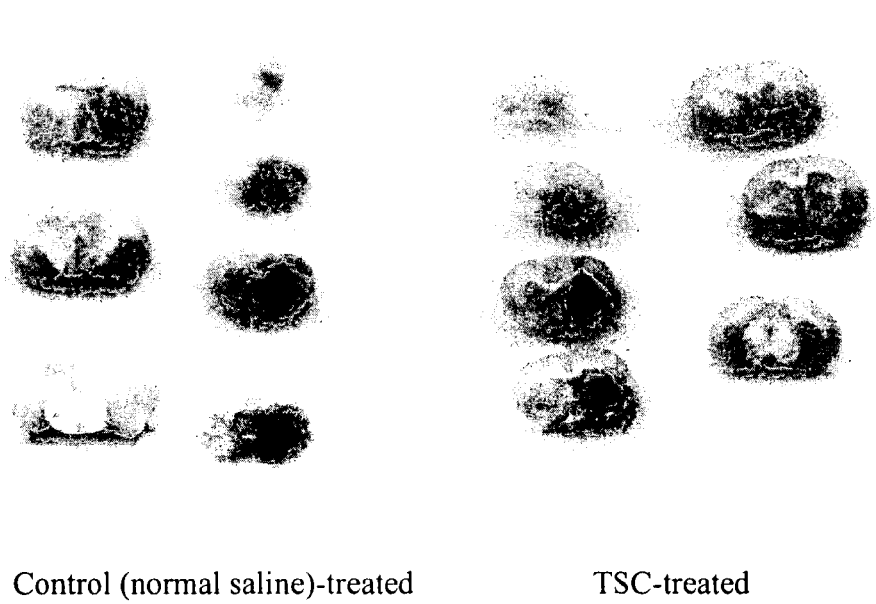
Control (normal saline)-treated          TSC-treated
Figure 6: Examples of Hematomas from Collagenase-Injection ICH Model

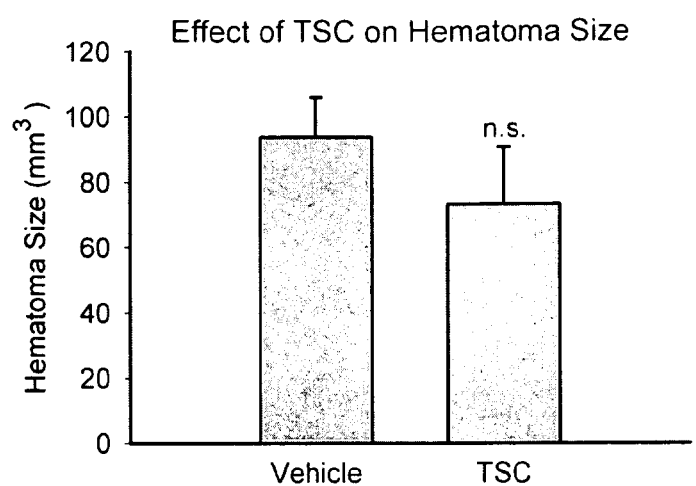
Figure 7 Effect of TSC on Hematoma Size
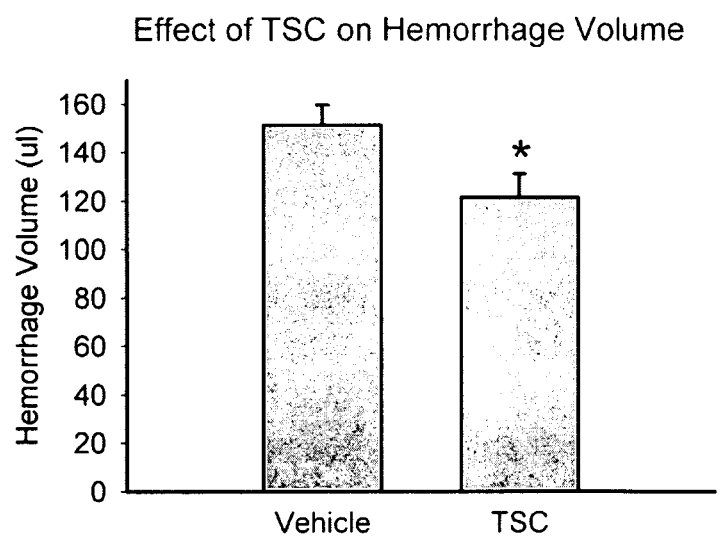
Figure 8 Effect of TSC on Hemorrhagic Volume

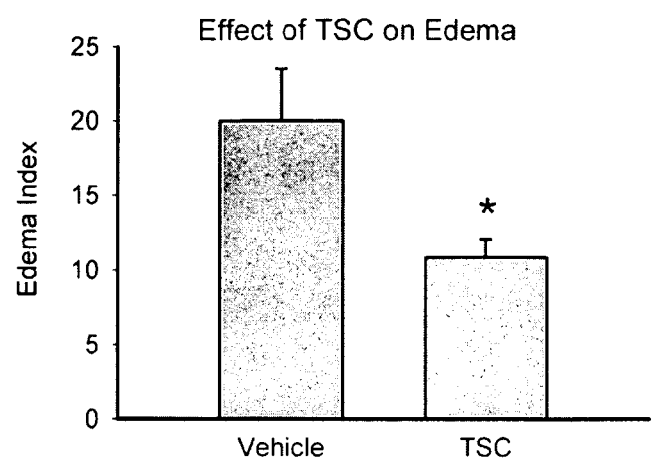
Figure 9 Effect of TSC on Tissue Edema

DIFFUSION ENHANCING COMPOUNDS AND THEIR USE ALONE OR WITH THROMBOLYTICS

This application is a continuation application of U.S. patent application Ser. No. 12/801,726, filed on Jun. 22, 2010, which claims benefit of, and priority from, U.S. Provisional Application Ser. No. 61/213,575 filed on Jun. 22, 2009, the entire contents of which are hereby incorporated by reference in this application.

FIELD OF THE INVENTION

The subject invention relates to diffusion enhancing compounds and their use, either alone or with thrombolytic agents, for the treatment of disorders resulting from the formation of a thrombus such as a myocardial infarction or stroke.

BACKGROUND OF THE INVENTION

A thrombus is the inappropriate activation of the hemostatic process in an uninjured or slightly injured vessel. A thrombus in a large blood vessel (mural thrombus) will decrease blood flow through that vessel. In a small blood vessel (occlusive thrombus), blood flow may be completely cut-off resulting in death of tissue supplied by that vessel. If a thrombus dislodges and becomes free-floating, it is termed as an embolus.

Some of the conditions which elevate risk of blood clots developing include atrial fibrillation (a form of cardiac arrhythmia), heart valve replacement, a recent heart attack, extended periods of inactivity-(see deep venous thrombosis below), and genetic or disease-related deficiencies in the blood's clotting abilities.

Blood clot prevention and treatment reduces the risk of stroke, heart attack and pulmonary embolism. Heparin and warfarin are often used to inhibit the formation and growth of existing thrombi; they are able to decrease blood coagulation by inhibiting vitamin K epoxide reductase, an enzyme needed to form mature clotting factors.

Acute ischemic stroke (AIS) is a potentially devastating disease that goes untreated in greater than 95% of patients. Acute ischemic stroke is estimated to affect more than 700,000 patients each year in the USA and 15 million worldwide [1,2]. New pharmacological therapeutics that can reduce the clinical deficits associated with AIS are needed. Ischemic stroke results from an obstruction within a blood vessel supplying blood to the brain.

Hemorrhagic stroke accounts for about 17 percent of stroke cases. It occurs when a weakened blood vessel ruptures.

Tissue plasminogen activator (tPA) is a protein thrombolytic agent (clot-busting drug). It is approved for use in certain patients having a heart attack or stroke. The drug can dissolve blood clots, which cause most heart attacks and strokes. tPA is the only drug approved by the U.S. Food and Drug Administration for the acute (urgent) treatment of ischemic stroke. Specifically, it is approved for the treatment of ischemic stroke in the first three hours after the start of symptoms [3].

If given promptly, tPA can significantly reduce the effects of ischemic stroke and reduce permanent disability. However, a time delay in starting tPA treatment often occurs because, when a patient presents with stroke-like symptoms, it is not immediately apparent whether the stroke has been caused by blood clots (ischemic stroke) or by a ruptured blood vessel (hemorrhagic stroke). tPA can only be given for ischemic strokes; therefore, the type of stroke must be determined before tPA is administered.

Although over 80% of all strokes are ischemic strokes, tPA or any thrombolytic, cannot be given immediately since it is possible that it could cause the hemorrhagic strokes to produce even worse effects. Determining whether a given patient has suffered a hemorrhagic or ischemic stroke is a time-consuming diagnosis which stands as a "gate" to immediate treatment. That, coupled with the fact that tPA must be given within 3 hours of the first symptoms, has resulted in only a small fraction of stroke patients receiving tPA.

tPA is effective in numerous preclinical models of acute ischemic stroke including the rabbit small clot embolic stroke model (RSCEM), [4] a useful tool and possibly a predictor of effective treatments that may eventually translate into functional efficacy in human clinical trials [2,4-7]. The primary endpoint used when assessing treatment efficacy in the RSCEM is functional behavior, which is based upon motor function components of the National Institute of Health Stroke Scale (NIHSS) for stroke in humans [8, 9].

Cerebral edema is the presence of excess fluid within either the cells or the extracellular spaces of the brain. This disorder also causes brain swelling and a rise in intracranial pressure. Head injuries, encephalitis, abscesses, lack of oxygen, tumors, strokes, and toxic agents are the most common causes of cerebral edema. Current treatment approaches to-cerebral edema can include mannitol, diuretics and corticosteroids. One of the main corticosteroids used is dexamethasone (Decadron).

Carotenoids are a class of hydrocarbons consisting of isoprenoid units. The backbone of the molecule consists of conjugated carbon-carbon double and single bonds, and can have pendant groups. Carotenoids such as crocetin and trans sodium crocetinate (TSC) are known to increase the diffusivity of oxygen in water.

U.S. Pat. No. 6,060,511 relates to trans sodium crocetinate (TSC) and its uses. The patent covers various uses of TSC such as improving oxygen diffusivity and treatment of hemorrhagic shock.

U.S. patent application Ser. No. 10/647,132 relates to synthesis methods for making bipolar trans carotenoids (BTC), including bipolar trans carotenoid salts (BTCS), and methods of using them.

U.S. patent application Ser. No. 11/361,054 relates to improved BTC synthesis methods and novel uses of the BTC.

U.S. patent application Ser. No. 12/081,236 relates to the use of bipolar trans carotenoids as a pretreatment and in the treatment of peripheral vascular disease.

U.S. application Ser. No. 12/289,713 relates to a new class of therapeutics that enhance small molecule diffusion.

SUMMARY OF THE INVENTION

The subject invention relates to a method of treating a mammal having an ischemic stroke, myocardial infarction, pulmonary embolism, or deep vein thrombosis comprising; administering a diffusion enhancing compound to said mammal, and administering a thrombolytic agent to said mammal. The invention also relates to a method of treating a mammal having a stroke where it is unknown whether the stroke is an ischemic stroke or a hemorrhagic stroke comprising: i) administering a diffusion enhancing compound to said mammal, ii) determining whether the stroke is an ischemic stroke, and if so determined, iii) administering a thrombolytic agent to said mammal.

The invention also relates to a method of treating a mammal having a hemorrhagic stroke, cerebral edema, or TIA comprising administering a diffusion enhancing compound to said mammal.

BRIEF DESCRIPTION OF THE FIGURES

FIG. 3 is a bar graph for single drug treatment.

FIG. 4 is a bar graph for combination therapy versus single drug therapy.

FIG. 5 is a bar graph concerning various treatments at one hour.

FIG. 6 depicts examples of hematomas from Collagenase-Injection ICH Model.

FIG. 7 is a bar graph of the effect of TSC on hematoma size.

FIG. 8 is a bar graph of the effect of TSC on hemorrhagic volume.

FIG. 9 is a bar graph of the effect of TSC on tissue edema.

DETAILED DESCRIPTION OF THE INVENTION

Figure 1:
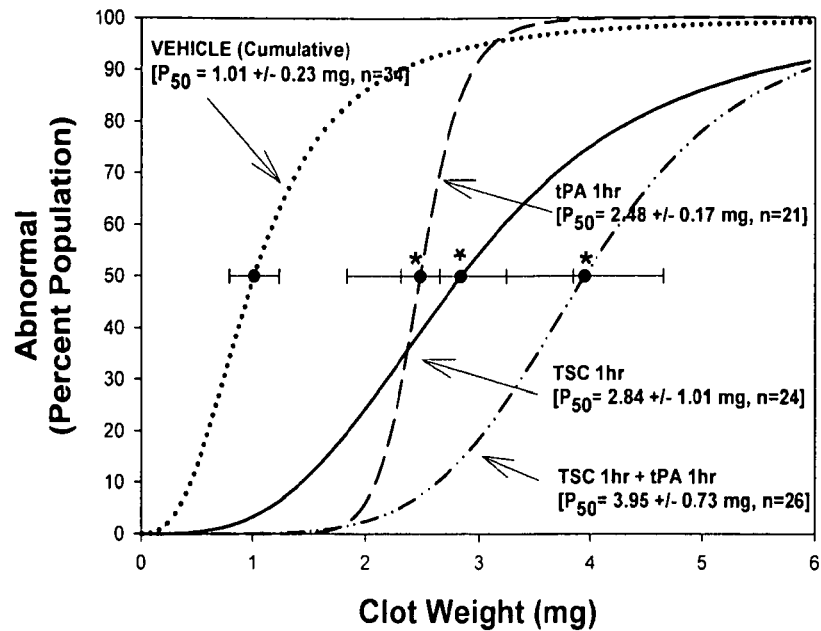
FIG. 1 provides the quantal curve for the effect of TSC on behavior.

The subject invention relates to diffusion enhancing compounds and their use with thrombolytic agents for the treatment of disorders resulting from the formation of a thrombus such as a myocardial infarction or stroke.
Compounds and Compositions of the Invention
Thrombolytics Thrombolysis is used in myocardial infarction (heart attack), ischemic strokes, deep vein thrombosis and pulmonary embolism to clear a blocked artery, i.e. a thrombus, and avoid permanent damage to the affected tissue (e.g. myocardium, brain, leg) and death. A less frequent use is to clear blocked catheters that are used in long-term medical therapy.

It should be noted that thrombolytic therapy in hemorrhagic strokes is contraindicated, as its use in that situation would prolong bleeding into the intracranial space and cause further damage.

The thrombolytic drugs include:
tissue plasminogen activator—t-PA—alteplase (Activase)
reteplase (Retavase)
tenecteplase (TNKase)
anistreplase (Eminase)
streptokinase (Kabikinase, Streptase)
urokinase (Abbokinase)
These drugs are most effective if administered immediately after it has been determined they are clinically appropriate. The drugs can be given in combination with intravenous heparin, or low molecular weight heparin, which are anticoagulant drugs.
Diffusion Enhancing Compounds The diffusion enhancing compounds of the invention include those compounds described in U.S. Ser. No. 10/647,132, U.S. Ser. No. 11/361,054, U.S. Ser. No. 12/081,236 and U.S. Ser. No. 12/289,713, each of which is hereby incorporated by reference in its entirety.

Included are bipolar trans carotenoid compounds having the formula: YZ-TCRO-ZY
where:
Y=a cation
Z=a polar group which is associated with the cation, and
TCRO=trans carotenoid skeleton,
such as TSC.

More specifically, the subject invention relates to trans carotenoids including trans carotenoid diesters, dialcohols, diketones and diacids, bipolar trans carotenoids (BTC), and bipolar trans carotenoid salts (BTCS) compounds and synthesis of such compounds having the structure:

where:
Y (which can be the same or different at the two ends)=H or a cation other than H, preferably Na+ or K+ or Li+. Y is advantageously a monovalent metal ion. Y can also be an organic cation, e. g., $R_4N^+$, $R_3S^+$, where R is H, or $C_nH_{2n+1}$ where n is 1-10, advantageously 1-6. For example, R can be methyl, ethyl, propyl or butyl.

Z (which can be the same or different at the two ends)=polar group which is associated with H or the cation. Optionally including the terminal carbon on the carotenoid (or carotenoid related compound), this group can be a carboxyl ($COO^-$) group or a CO group (e.g. ester, aldehyde or ketone group), or a hydroxyl group. This group can also be a sulfate group ($OSO_3^-$) or a monophosphate group ($OPO_3^-$), ($OP(OH)O_2^-$), a diphosphate group, triphosphate or combinations thereof. This group can also be an ester group of COOR where the R is $C_nH_{2n-1}$.

TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups (X) are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis (also known as "Z"); if they are on the opposite side of the carbon-carbon bond, they are designated as trans (also known as "E"). Throughout this case, the isomers will be referred to as cis and trans.

The compounds of the subject invention are trans. The cis isomer typically is a detriment—and results in the diffusivity not being increased. In one embodiment, a cis isomer can be utilized where the skeleton remains linear. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The pendant groups X (which can be the same or different) are hydrogen (H) atoms, or a linear or branched hydrocarbon group having 10 or less carbons, advantageously 4 or less, (optionally containing a halogen), or a halogen. X could also be an ester group (COO—) or an ethoxy/methoxy group. Examples of X are a methyl group ($CH_3$), an ethyl group ($C_2H_5$), a phenyl or single aromatic ring structure with or without pendant groups from the ring, a halogen-containing alkyl group (C1-C10) such as $CH_2Cl$, or a halogen such as Cl or Br or a methoxy ($OCH_3$) or ethoxy ($OCH_2CH_3$). The pendant groups can be the same or different but the pendant groups utilized must maintain the skeleton as linear.

Although many carotenoids exist in nature, carotenoid salts do not. Commonly-owned U.S. Pat. No. 6,060,511 hereby incorporated by reference in its entirety, relates to trans sodium crocetinate (TSC). The TSC was made by reacting naturally occurring saffron with sodium hydroxide followed by extractions that selected primarily for the trans isomer.

The presence of the cis and trans isomers of a carotenoid or carotenoid salt can be determined by looking at the ultraviolet-visible spectrum for the carotenoid sample dissolved in an aqueous solution. Given the spectrum, the value of the absorbence of the highest peak which occurs in the visible wave length range of 380 to 470 nm (the number depending on the solvent used and the chain length of the BTC or BTCS. The addition of pendant groups or differing chain lengths will change this peak absorbance but someone skilled in the art will recognize the existence of an absorbance peak in the visible range corresponding to the conjugated backbone structure of these molecules.) is divided by the absorbency of the peak which occurs in the UV wave length range of 220 to 300 nm can be used to determine the purity level of the trans isomer. When the trans carotenoid diester (TCD) or BTCS is dissolved in water, the highest visible wave length range peak will be at between 380 nm to 470 nm (depending on the exact chemical structure, backbone length and pendant groups) and the UV wave length range peak will be between 220 to 300 nm. According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis, using a cuvette designed for UV and visible wavelength ranges, on the trans sodium salt of crocetin of commonly owned U.S. Pat. No. 6,060,511 (TSC made by reacting naturally occurring saffron with sodium hydroxide followed by extractions which selected primarily for the trans isomer), the value obtained averages about 6.8. Performing that test on the synthetic TSC of the subject invention, that ratio is greater than 7.0 (e.g. 7.0 to 8.5), advantageously greater than 7.5 (e.g. 7.5-8.5), most advantageously greater than 8. The synthesized material is a "purer" or highly purified trans isomer.

Formulation and Administration of the Compounds and Compositions of the Invention A detailed description of formulation and administration of diffusing enhancing compounds can be found in commonly owned applications U.S. Ser. No. 12/081,236 and U.S. Ser. No. 12/289,713, each of which is hereby incorporated by reference in its entirety.

A diffusion enhancing compound such as TSC can be administered by various routes. For example, the compound which can be formulated with other compounds including excipients, can be administered at the proper dosage as an intravenous injection or infusion, an intramuscular injection, or in an oral form.

The IV injection route is an advantageous route for giving TSC for the uses of the subject application since the patient may well be unconscious. Typically, a diffusion enhancing compound such as TSC is administered as soon as possible if a thrombus is believed present or if the patient is hemorrhaging.

Cyclodextrins

In order to administer some pharmaceuticals, it is necessary to add another compound which will aid in increasing the absorption/solubility/concentration of the active pharmaceutical ingredient (API). Such compounds are called excipients, and cyclodextrins are examples of excipients. Cyclodextrins are cyclic carbohydrate chains derived from starch. They differ from one another by the number of glucopyranose units in their structure. The parent cyclodextrins contain six, seven and eight glucopyranose units, and are referred to as alpha, beta and gamma cyclodextrins respectively. Cyclodextrins were first discovered in 1891, and have been used as part of pharmaceutical preparations for several years.

Cyclodextrins are cyclic (alpha-1,4)-linked oligosaccharides of alpha-D-glucopyranose containing a relatively hydrophobic central cavity and hydrophilic outer surface. In the pharmaceutical industry, cyclodextrins have mainly been used as complexing agents to increase the aqueous solubility of poorly water-soluble drugs, and to increase their bioavailability and stability. In addition, cyclodextrins are used to reduce or prevent gastrointestinal or ocular irritation, reduce or eliminate unpleasant smells or tastes, prevent drug-drug or drug-additive interactions, or even to convert oils and liquid drugs into microcrystalline or amorphous powders.

Although the BTC compounds are soluble in water, the use of the cyclodextrins can increase that solubility even more so that a smaller volume of drug solution can be administered for a given dosage.

There are a number of cyclodextrins that can be used with the Compounds of the Invention. See for example, U.S. Pat. No. 4,727,064, hereby incorporated by reference in its entirety. Advantageous cyclodextrins are γ-cyclodextrin, 2-hydroxylpropyl-γ-cyclodextrin and 2-hydroxylpropyl-β-cyclodextrin, or other cyclodextrins which enhance the solubility of the BTC.

The use of gamma-cyclodextrin with TSC increases the solubility of TSC in water by 3-7 times. Although this is not as large a factor as seen in some other cases for increasing the solubility of an active agent with a cyclodextrin, it is important in allowing for the parenteral administration of TSC in smaller volume dosages to humans (or animals). Dosages of TSC and gamma-cyclodextrin have resulted in aqueous solutions containing as much as 44 milligrams of TSC per ml of solution, with an advantageous range of 20-30 mg/ml of solution. The solutions need not be equalmolar. The incorporation of the gamma cyclodextrin also allows for TSC to be absorbed into the blood stream when injected intramuscularly. Absorption is quick, and efficacious blood levels of TSC are reached quickly (as shown in rats).

The cyclodextrin formulation can be used with other trans carotenoids and carotenoid salts. The subject invention also includes novel compositions of carotenoids which are not salts (e.g. acid forms such as crocetin, crocin or the intermediate compounds noted above) and a cyclodextrin. In other words, trans carotenoids which are not salts can be formulated with a cyclodextrin. Mannitol can be added for osmolality, or the cyclodextrin BTC mixture can be added to isotonic saline (see below).

The amount of the cyclodextrin used is that amount which will contain the trans carotenoid but not so much that it will not release the trans carotenoid. Advantageously, the ratio of cyclodextrin to BTC, e.g., TSC, is 4 to 1 or 5 to 1. See also U.S. Patent Application No. 61/350,804, the content of which is hereby incorporated by reference in its entirety.

Cyclodextrin-Mannitol

A trans carotenoid such as TSC can be formulated with a cyclodextrin as noted above and a non-metabolized sugar such as mannitol (e.g. d-mannitol to adjust the osmotic pressure to be the same as that of blood). Solutions containing over 20 mg TSC/ml of solution can be made this way. This solution can be added to isotonic saline or to other isotonic solutions in order to dilute it and still maintain the proper osmolality.

Mannitol/Acetic Acid

A BTCS such as TSC can be formulated with mannitol such as d-mannitol, and a mild buffering agent such as acetic acid or citric acid to adjust the pH. The pH of the solution should be around 8 to 8.5. It should be close to being an isotonic solution, and, as such, can be injected directly into the blood stream.

Water+Saline

A BTCS such as TSC can be dissolved in water (advantageously injectable water). This solution can then be diluted with water, normal saline, Ringer's lactate or phosphate buffer, and the resulting mixture either infused or injected.

Buffers

A buffer such as glycine, bicarbonate, or sodium carbonate can be added to the formulation at a level of about 50 mM for stability of the BCT such as TSC.

TSC and Gamma-Cyclodextrin

The ratio of TSC to cyclodextrin is based on TSC:cyclodextrin solubility data. For example, 20 mg/ml TSC, 8% gamma cyclodextrin, 50 mM glycine, 2.33% mannitol with pH 8.2+/−0.5, or 10 mg/ml TSC and 4% cyclodextrin, or 5 mg/ml and 2% cyclodextrin. The ratios of these ingredients can be altered somewhat, as is obvious to one skilled in this art.

Mannitol can be used to adjust osmolality and its concentration varies depending on the concentration of other ingredients. The glycine is held constant. TSC is more stable at higher pHs. pH of around 8.2+/−0.5 is required for stability and physiological compatibility. The use of glycine is compatible with lyophilization. Alternatively, the TSC and cyclodextrin is formulated using a 50 mM bicarbonate buffer in place of the glycine.

Endotoxin Removal of Gamma-Cyclodextrin

Commercially available pharmaceutical grade cyclodextrin has endotoxin levels that are incompatible with intravenous injection. The endotoxin levels must be reduced in order to use the cyclodextrin in a BTC formulation intended for intravenous injection.

After it is determined that a thrombus is present, a therapeutically effective amount, i.e. a clot dissolving amount, of the thrombolytic agent such as tPA, can also be administered. Formulation of thrombolytics is well known to those skilled in the art. A thrombolytic such as tPA, is typically administered via IV injection. If a diffusion enhancing drug has been administered, the advantage of administration of a thrombolytic is highest within the first ninety minutes, but can extend up to 6, 9 or even 12 hours after the start of symptoms.

Thrombolytic and/or diffusion enhancing drugs also can be given in combination with intravenous heparin, or low molecular weight heparin, which are anticoagulant drugs. Heparin and warfarin are often used to inhibit the formation and growth of existing thrombi.

In one embodiment, the thrombolytic agent is formulated together with the diffusion enhancing compound for IV administration.

Uses of the Compounds and Compositions of the Invention

A diffusion enhancing compound such as trans sodium crocetinate (TSC) can be administered either alone or in combination with the thrombolytic such as tissue plasminogen activator (tPA), to reduce deficits associated with a thrombosis.

Stroke

For a given isolated blood vessel, blood flow to the brain tissue can be hampered in two ways:
1. the vessel clogs within (ischemic stroke)
2. the vessel ruptures, causing blood to leak into the brain (hemorrhagic stroke)

A beneficial treatment for stroke would be:
(1) A drug which can be used for treating either a hemorrhagic stroke or an ischemic stroke, or
(2) A drug which can increase the window for giving a thrombolytic, e.g. the approved 3-hour window of time for giving tPA.

Ischemic Stroke

Ischemic stroke accounts for about 83 percent of all cases. Ischemic strokes occur as a result of an obstruction within a blood vessel supplying blood to the brain. The underlying condition for this type of obstruction is the development of fatty deposits lining the vessel walls. This condition is called atherosclerosis. These fatty deposits are associated with two types of obstruction:

Cerebral thrombosis refers to a thrombus (blood clot) that develops at the clogged part of the vessel.

Cerebral embolism refers generally to a blood clot that forms at another location in the circulatory system, usually the heart and large arteries of the upper chest and neck. A portion of the blood clot breaks loose, enters the bloodstream and travels through the brain's blood vessels until it reaches vessels too small to let it pass. A second important cause of embolism is an irregular heartbeat, known as atrial fibrillation. It creates conditions where clots can form in the heart, dislodge and travel to the brain.

Also called TIAs, transient ischemic attacks are minor or warning strokes. In a TIA, conditions indicative of an ischemic stroke are present and the typical stroke warning signs develop. However, the symptoms occur for a short time and tend to resolve through normal mechanisms. Even though the symptoms disappear after a short time, TIAs may be indicators of a possible major stroke. Steps should be taken immediately to prevent an ischemic stroke. A patient showing signs of a TIA or at risk of a stroke should be given a diffusion enhancing compound such as TSC, e.g., by IV injection or orally at a dosage in the range of 0.1-2 mg/kg.

In order to find new drugs for stoke victims, different animal models of ischemic stroke are used. In one model, blood vessels (middle cerebral artery, two carotid arteries) are ligated for a period of 2 hours. The ligature is then removed, a drug is given, and the animals (rats in this case) are sacrificed after 24 hours. The brain sections are stained and examined in order to determine the amount of damaged (ischemic) tissue. With this model, it was found that a TSC dosage of 0.1 mg/kg in the rats produced a profound (about 60%) reduction in the amount of ischemic tissue.

In a rat model of hemorrhagic shock, in which the enzyme collagenase is used to cause the blood vessels to leak into the brain, it was found that the administration of 0.1 mg/kg of TSC did not increase the amount of blood that hemorrhages into the brain. In fact, it caused a decrease in that hemorrhage volume. Of perhaps more importance, it was found that TSC reduced the amount of edema caused by the hemorrhagic stroke by about 50%. Thus, TSC appears to be a drug which meets category (1) above: a drug which can be used on either type of stroke without fear of causing further damage.

The combination of TSC and tPA effectively improves functional behavior using the RSCEM model discussed below. RSCEM is produced by injection of blood clots into the cerebral vasculature of a rabbit to produce cerebral ischemia resulting in behavioral deficits that can be measured quantitatively using a dichotomous rating scale and a statistical quantal analysis technique.

Example 1 below shows that TSC administration significantly improves clinical rating scores when administered within 1 hour of embolization in the RSCEM model. Moreover, the study shows that TSC can be administered safely in combination with the thrombolytic tPA and that combination therapy also produces a significant functional behavioral improvement in embolized rabbits. Simultaneous administration of TSC and tPA is beneficial for treating heart attacks caused by clots, as is giving TSC alone.

The early use of a diffusion enhancing compound such as TSC can increase the window of opportunity of giving a thrombolytic agent such as tPA later in order to treat ischemic strokes. The data teaches that TSC can extend the treatment window for tPA to at least 3 hours in the RSCEM model, a time at which tPA alone is ineffective in this animal model. This time is believed to be multiplied by a factor of 3 to 4 in humans. Thus, if a diffusion enhancing compound such as TSC is given to a human within the first 3-4 hours after the first stoke symptoms, then a thrombolytic agent such as tPA can be given 9 or even up to 12 hours after the first stroke symptoms. A patient showing signs of an ischemic stroke should be given a diffusion enhancing compound such as TSC, e.g., by IV injection or infusion, or orally, at a dosage in the range of 0.1-2 mg/kg. Treatment with TSC alone is also an effective treatment for stroke.

Hemorrhagic Stroke

Hemorrhagic stroke accounts for about 17 percent of stroke cases. It results from a weakened vessel that ruptures and bleeds into the surrounding brain. The blood accumulates and compresses the surrounding brain tissue. The two types of hemorrhagic strokes are intracerebral hemorrhage or subarachnoid hemorrhage.

Hemorrhagic stroke occurs when a weakened blood vessel ruptures. Two types of weakened blood vessels usually cause hemorrhagic stroke: aneurysms and arteriovenous malformations (AVMs). An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. Any one of these vessels can rupture, also causing bleeding into the brain.

A diffusion enhancing compound such as a BTCS compounds (e.g. TSC), can be used in treatment of hemorrhagic stroke. The compound can be administered by various routes, including IV injection or infusion or orally. The IV injection or infusion route is an advantageous route for giving a diffusion enhancing compound for hemorrhagic stroke since the patient may well be unconscious. Typically, a diffusion enhancing compound such as TSC is administered as soon as possible if the patient is hemorrhaging, but can also be given after the hemorrhage has subsided. A patient showing signs of a hemorrhagic stroke should be given a diffusion enhancing compound such as TSC, e.g., by IV injection or infusion, or orally, at a dosage in the range of 0.1-2 mg/kg.

Cerebral Edema

Cerebral edema is an excess accumulation of water in the intracellular and/or extracellular spaces of the brain. Four types of cerebral edema have been distinguished:

(1) Vasogenic Cerebral Edema

This is due to a breakdown of tight endothelial junctions which make up the blood-brain barrier (BBB). This allows normally excluded intravascular proteins and fluid to penetrate into cerebral parenchymal extracellular space. Once plasma constituents cross the BBB, the edema spreads; this may be quite fast and widespread. As water enters white matter it moves extracellularly along fiber tracts and can also affect the gray matter. This type of edema is seen in response to trauma, tumors, focal inflammation, late stages of cerebral ischemia and hypertensive encephalopathy.

Some of the mechanisms contributing to BBB dysfunction are: physical disruption by arterial hypertension or trauma, tumor-facilitated release of vasoactive and endothelial destructive compounds (e.g. arachidonic acid, excitatory neurotransmitters, eicosanoids, bradykinin, histamine and free radicals). Some of the special subcategories of vasogenic edema include:

A. Hydrostatic Cerebral Edema

This form of cerebral edema is seen in acute, malignant hypertension. It is thought to result from direct transmission of pressure to cerebral capillary with transudation of fluid into the extra-cellular fluid from the capillaries.

B. Cerebral Edema from Brain Cancer

Cancerous glial cells (glioma) of the brain can increase secretion of vascular endothelial growth factor (VEGF) which weakens the junctions of the blood-brain barrier. Dexamethasone (a corticosteroid compound) can be of benefit in reducing VEGF secretion.

C. High Altitude Cerebral Edema

High altitude cerebral edema (or HACE) is a severe form of (sometimes fatal) altitude sickness. HACE is the result of swelling of brain tissue from leakage of fluids from the capillaries due to the effects of hypoxia on the mitochondria-rich endothelial cells of the blood-brain barrier.

Symptoms can include headache, loss of coordination (ataxia), weakness, and decreasing levels of consciousness including disorientation, loss of memory, hallucinations, psychotic behavior, and coma. It generally occurs after a week or more at high altitude. Severe instances can lead to death if not treated quickly. Immediate descent is a necessary life-saving measure (2,000-4,000 feet). There are some medications (e.g. dexamethasone) that may be prescribed for treatment but these require proper medical training in their use. Anyone suffering from HACE must be evacuated to a medical facility for proper follow-up treatment. Climbers may also suffer high altitude pulmonary edema (HAPE), which affects the lungs. While not as life threatening as HACE in the initial stages, failure to descend to lower altitudes or receive medical treatment can also lead to death.

(2) Cytotoxic Cerebral Edema

In this type of edema the BBB remains intact. This edema is due to the derangement in cellular metabolism resulting in inadequate functioning of the sodium and potassium pump in the glial cell membrane. As a result there is cellular retention of sodium and water. There are swollen astrocytes in gray and white matter. Cytoxotic edema is seen with various intoxications (dinitrophenol, triethyltin, hexachlorophene, isoniazid), in Reye's syndrome, severe hypothermia, early ischemia, encephalopathy, early stroke or hypoxia, cardiac arrest, pseudotumor cerebri, and cerebral toxins.

(3) Osmotic Cerebral Edema

Normally cerebral-spinal fluid (CSF) and extracellular fluid (ECF) osmolality of the brain is slightly greater than that of plasma. When plasma is diluted by excessive water intake (or hyponatremia), syndrome of inappropriate antidiuretic hormone secretion (SIADH), hemodialysis, or rapid reduction of blood glucose in hyperosmolar hyperglycemic state (HHS), formerly hyperosmolar non-ketotic acidosis (HONK), the brain osmolality will then exceed the serum osmolality creating an abnormal pressure gradient down which water will flow into the brain causing edema.

(4) Interstitial Cerebral Edema

Interstitial cerebral edema occurs in obstructive hydrocephalus. This form of edema is due to rupture of CSF-brain barrier: permits CSF to penetrate brain and spread in the extracellular space of white matter. Differentiated from vasogenic edema in that fluid contains almost no protein.

A diffusion enhancing compound such as a BTCS compounds (e.g. TSC), can be used in treatment of cerebral edema. The compound can be administered by various routes, including IV injection or orally. The IV injection route is an advantageous route for giving TSC for cerebral edema since the patient may well be unconscious. Typically, a diffusion enhancing compound such as TSC is administered as soon as a cerebral edema is detected. A patient showing signs of a cerebral edema should be given a diffusion enhancing compound such as TSC, e.g., by IV injection or infusion, or orally, at a dosage in the range of 0.1-2 mg/kg.

In another embodiment, cerebral edema treatment can include one or more of mannitol, diuretics and corticosteroids. An advantageous corticosteroid is dexamethasone.

Myocardial Infarction

Myocardial infarction (MI or AMI for acute myocardial infarction), commonly known as a heart attack, occurs when the blood supply to part of the heart is interrupted causing some heart cells to die. This is most commonly due to occlusion (blockage) of a coronary artery following the rupture of a vulnerable atherosclerotic plaque, which is an unstable collection of lipids (like cholesterol) and white blood cells (especially macrophages) in the wall of an artery. The resulting ischemia (restriction in blood supply) and oxygen shortage, if left untreated for a sufficient period of time, can cause damage and/or death (infarction) of heart muscle tissue (myocardium).

A diffusion enhancing compound such as a BTCS compounds (e.g. TSC), can be used, either alone or in conjunction with a thrombolytic, as a treatment for myocardial infarction. A diffusion enhancing compound such as TSC can be administered by various routes. For example, the compound which can be formulated with other compounds, can be administered at the proper dosage as an intravenous injection or infusion, an intramuscular injection, or in an oral form. The IV injection route is an advantageous route for giving a diffusion enhancing compound such as TSC for myocardial infarction since the patient may well be unconscious. Typically, the compound is administered as soon as possible. A patient showing signs of a myocardial infarction should be given a diffusion enhancing compound such as TSC, e.g., by IV injection or infusion, or orally, at a dosage in the range of 0.1-2 mg/kg.

If a thrombus is believed to be present, a therapeutically effective amount, i.e. a clot dissolving amount, of the thrombolytic agent such as tPA, can also be administered. Formulations of thrombolytics are well known to those skilled in the art. A thrombolytic such as tPA, is typically administered via IV injection. If a diffusion enhancing drug has been administered, the advantage of administration of a thrombolytic is highest within the first ninety minutes, but can extend up to 9 or even 12 hours after the start of symptoms.

Thrombolytic drugs can be given in combination with intravenous heparin, or low molecular weight heparin, which are anticoagulant drugs.

Deep Vein Thrombosis

Deep vein thrombosis (also known as deep-vein thrombosis or deep venous thrombosis) is the formation of a blood clot ("thrombus") in a deep vein. It is a form of thrombophlebitis (inflammation of a vein with clot formation).

Deep vein thrombosis commonly affects the leg veins (such as the femoral vein or the popliteal vein) or the deep veins of the pelvis. Occasionally the veins of the arm are affected (if spontaneous, this is known as Paget-Schrotter disease).

A diffusion enhancing compound such as a BTCS compounds (e.g. TSC), can be used in conjunction with a thrombolytic as a treatment for deep vein thrombosis. A diffusion enhancing compound such as a BTCS compounds (e.g. TSC), can be used in conjunction with a thrombolytic as a treatment for deep vein thrombosis. A diffusion enhancing compound such as TSC can be administered by various routes. For example, the compound which can be formulated with other compounds (excipients), can be administered at the proper dosage as an intravenous injection or infusion, an intramuscular injection, or in an oral form.

The IV injection route is an advantageous route for giving a diffusion enhancing compound such as TSC for deep vein thrombosis since the patient may well be unconscious. Typically, the compound is administered as soon as possible. A patient showing signs of a deep vein thrombosis should be given a diffusion enhancing compound such as TSC, e.g., by IV injection or infusion, or orally, at a dosage in the range of 0.1-2 mg/kg.

A therapeutically effective amount, i.e. a clot dissolving amount, of the thrombolytic agent such as tPA, can also be administered. Formulation of thrombolytics are well known to those skilled in the art. A thrombolytic such as tPA, is typically administered via IV injection. If a diffusion enhancing drug has been administered, the advantage of administration of a thrombolytic is highest within the first ninety minutes, but can extend up to 9 or even 12 hours after the start of symptoms.

Thrombolytic drugs can be given in combination with intravenous heparin, or low molecular weight heparin, which are anticoagulant drugs.

Pulmonary Embolism

Pulmonary embolism (PE) is a blockage of the pulmonary artery or one of its branches, usually occurring when a deep vein thrombus (blood clot from a vein) becomes dislodged from its site of formation and travels, or embolizes, to the arterial blood supply of one of the lungs. This process is termed thromboembolism.

A diffusion enhancing compound such as a BTCS compounds (e.g. TSC), can be used, either alone or in conjunction with a thrombolytic, as a treatment for pulmonary embolism. The compound can be administered by various routes. For example, the compound which can be formulated with other compounds, can be administered at the proper dosage as an intravenous injection or infusion, an intramuscular injection, or in an oral form.

The IV injection route is an advantageous route for giving a diffusion enhancing compound such as TSC for pulmonary embolism since the patient may well be unconscious. Typically, the compound is administered as soon as possible. A patient showing signs of a pulmonary embolism should be given a diffusion enhancing compound such as TSC, e.g., by IV injection or infusion, or orally, at a dosage in the range of 0.1-2 mg/kg.

If a thrombus is believed to be present, a therapeutically effective amount, i.e. a clot dissolving amount, of the thrombolytic agent such as tPA, is administered. Formulation of thrombolytics are well known to those skilled in the art. A thrombolytic such as tPA, is typically administered via IV injection. If a diffusion enhancing drug has been administered, the advantage of administration of a thrombolytic is highest within the first ninety minutes, but can extend up to 9 or even 12 hours after the start of symptoms.

Thrombolytic drugs can be given in combination with intravenous heparin, or low molecular weight heparin, which are anticoagulant drugs.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

Trans Sodium Crocetinate with Tissue Plasminogen Activator in Ischemic Stroke

General Description of Animal Model:

Methods: This model uses rabbits and is known as RSCEM. Male New Zealand white rabbits were anesthetized using isoflurane (5% induction, 2% maintenance by facemask), the bifurcation of the right carotid artery was exposed and the external carotid was ligated just distal to the bifurcation, where a catheter was inserted into the common carotid and secured with ligatures. The incision was closed around the catheter with the distal ends left accessible outside the neck; the catheter was filled with heparinized saline and plugged with an injection cap. Rabbits were allowed to recover from anesthesia for a minimum of 2 h until they behaved normally. After that time, microdots were prepared from blood drawn from a donor rabbit and allowed to clot at 37° C., as described in detail previously [4,10,11]. Microclots were re-suspended in PBS, then washed and allowed to settle, followed by aspiration of the supernatant and spiking of the microclots with tracer quantities of 15-μm radiolabeled microspheres. The specific activity of the particles was determined by removing an aliquot, after which appropriate volumes of PBS solution were added so that a predetermined weight of clot particles were rapidly injected through the catheter and both the syringe and catheter were flushed with 5 ml of normal saline.

Quantal Dose-Response Analysis: For behavioral analysis, a quantal dose-response data analysis technique was used as described previously [4, 10, 11]. A wide range of lesion volumes is induced to generate both normal and abnormal animals with various behavioral deficits. Using 3 or more different doses of microdots generated each quantal analysis curve. In the absence of treatment, the low end of the curve (small numbers of microdots cause no grossly apparent neurologic dysfunction) and the high end (large numbers of microdots invariably cause encephalopathy or death). Each animal is rated as either normal or abnormal (including dead animals), and inter-rater variability is very low (<5%). Behaviorally normal rabbits did not have any signs of impairment, whereas behaviorally abnormal rabbits had loss of balance, head leans, circling, and/or limb paralysis. With this simple rating system, the composite result for a group of animals is quite reproducible. Briefly, to evaluate the quantitative relationship between numbers of clots in the brain and neurological deficits (coma or death), logistic (S-shaped) curves are fitted by computer to the quantal dose-response data (see FIGS. 1 and 2).

These parameters are measures of the amount of microclots (in mg) that produce neurologic dysfunction in 50% of a group of animals ($P_{50}$). The $P_{50}$ values are then calculated as described previously [4, 10, 11] and are presented as Mean±SEM. A separate curve is generated for each treatment condition tested. A statistically significant shift to the right of the quantal curve or an increase in the $P_{50}$ value is indicative of a behavioral improvement and neuroprotection. The data were analyzed using the t-test.

Specific Study Done:

Drug Treatment: For test substance administration, rabbits were placed in a Plexiglas restrainer for the duration of the treatment. Rabbits were given a bolus intravenous injection of vehicle or TSC (0.25 mg/kg) over 1 minute using the marginal ear vein at a dose of 0.22 ml/kg. For thrombolytic studies, tPA (3.3 mg/kg) was given 1 or 3 hours post-embolization, with 20% as a bolus IV injection over one minute, followed by the remainder infused over 30 min. Genentech, Inc. (South San Francisco, Calif.; Lots 745047, 705409) as described previously [4]. For the construction of quantal analysis, rabbits were included in the study if they were able to survive to receive treatment following embolization. All others were excluded from the study and further analysis.

Results:

(1) TSC Improves Behavior at 1 Hour Post-Embolization

In this series of studies, the effects of administration of TSC (0.25 mg/kg) on behavioral function measured 24 hours following embolization was determined. Using the RSCEM, TSC significantly ($p<0.05$) increased behavioral performance with a $P_{50}$ value of 2.84±1.01 mg (n=24) compared to the vehicle control ($P_{50}$=1.01±0.23 mg, n=34), FIG. 1 provides the quantal curve for the effect of TSC on behavior.

(2) TSC Combination Studies: tPA 1 Hour Delay

FIG. 1 also provides a graphical representation of the effects of tPA on behavior and the group $P_{50}$ value when given 1 hour following embolization. tPA significantly improved behavior and increased the group $P_{50}$ value of 2.48±0.17 mg (n=21, $p<0.05$) compared to the vehicle control group, which had a $P_{50}$ value of 1.01±0.23 mg (n=34). In combination studies, when both TSC and tPA were administered 1 hour following embolization, the group $P_{50}$ value measured 24 hour following embolization was 3.95±0.73 mg (n=26), a $P_{50}$ that was significantly different from control ($p<0.05$). There was a trend for a synergistic effect of the drug combination that did not reach statistical significance compared to TSC ($p=0.372$) or tPA ($p=0.087$).

(3) TSC Combination Studies: tPA 3 Hour Delay

Figure 2:
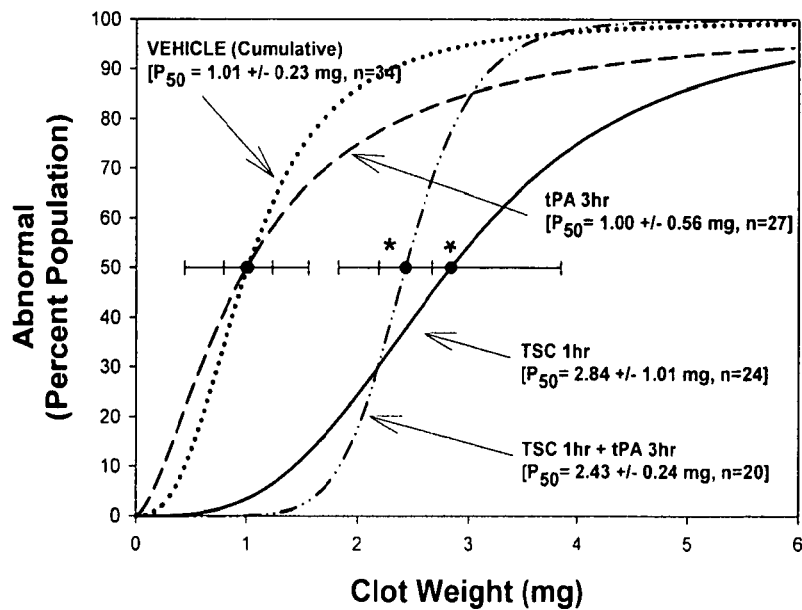
FIG. 2 provides a graphical representation of the effects of tPA on behavior and the Group $P_{50}$ value when given three hours following embolization.

FIG. 2 below provides a graphical representation of the effects of tPA on behavior and the group $P_{50}$ value when given 3 hours following embolization. tPA did not significantly improve behavior ($p>0.05$) resulting in a group $P_{50}$ value of 1.00±0.56 mg (n=27) compared to the vehicle control group, which had a $P_{50}$ value of 1.01±0.23 mg (n=34). In combination studies, when TSC was administered 1 hour following embolization and tPA was given 3 hours following embolization, the group $P_{50}$ value was 2.43±0.24 mg (n=20), a $P_{50}$ that was significantly different from control (p<0.05).

Summary of Results

FIGS. 1 and 2 show abnormal rabbits as a function of clot weight measured in brain. Results are shown as mean±SEM for the number of rabbits in each group (n). The curve labeled Vehicle (dotted line in FIGS. 1 and 2) shows that 50% of rabbits with a clot dose ($P_{50}$) value) of 1.01±0.23 mg (n=34) are abnormal. TSC (0.25 mg/kg) treatment (solid lines in FIGS. 1 and 2) 1 hour post-embolization increased the $P_{50}$ value to 2.84±0.51 mg (n=24, p>0.05). tPA (dashed lines in FIGS. 1 and 2) when administered 1 hour post-embolization significantly increased the $P_{50}$ value, but was ineffective when given 3 hours following embolization (FIG. 2, dashed line). The combination of TSC (1 hour) plus tPA (either 1 hour, FIG. 1) or (3 hours, FIG. 2) significantly improved behavior and increased $P_{50}$ values.

FIG. 3 also shows that TSC administration significantly improves clinical rating scores when administered within 1 hour of embolization. Moreover, the study shows that TSC may be administered safely in combination with the thrombolytic tPA (FIG. 4) and that combination therapy produces a significant behavioral improvement in embolized rabbits. The data teach that TSC can extend the treatment window for tPA to at least 3 hours in the RSCEM animal model, a time at which tPA alone is ineffective in this animal model. In addition, the data show that TSC administered alone at 1 hour post-embolization in this model is also statistically effective. Again, it is thought that the times in this rabbit model can by multiplied by a factor of 3 to 4 in order to estimate human times.

As mentioned previously, tPA is a treatment for heart attacks as well as strokes. Even though this animal model concerns an ischemic stroke, it may also offer some suggestions concerning a better treatment for heart attacks caused by clots. For example, the 1-hour data (FIG. 3) show an equal effect of TSC or tPA. In order to determine if those two drugs given together would exhibit an even better result, an additional study was done in which both drugs were injected at a time of 1 hour after the clots were injected into the rabbit brains. Those results are shown in FIG. 5.

All three drug treatments (tPA alone, TSC alone, tPA/TSC combination) provide a statistically-significant result in improving the condition of the rabbits. It is also interesting to see that the combination of the 2 drugs produced a benefit which appears to be better from either of the drugs given alone, although it is not statistically different from the individual drugs given alone. It should be noted, though, that tPA must be given within 3 hours of the first symptoms of a stroke, a time which limits its use. However, TSC can be given without knowing what type of stroke has occurred.

Example 2

Trans Sodium Crocetinate Treatment in Hemorrhagic Stroke

Background

A key risk of early intervention in ischemic stroke is that injury resulting from hemorrhagic stroke and/or hemorrhagic transformation might be aggravated, as is the case with tissue plasminogen activator (tPA) therapy. Therefore, the current study examined the effect of TSC in a model of intracranial hemorrhage (ICH) in order to evaluate whether early TSC treatment under conditions of hemorrhagic stroke adversely affects outcomes.

Twelve male, Sprague-Dawley rats (Taconic, Inc.), weighing between 250 to 300 Grams were fed ad libitum and maintained on a 12-hour light/dark cycle. The rats were randomly assigned to 1 of 2 groups as follows: TSC-treated group (n=6) receiving intravenous infusion of TSC (total dose 0.091 mg/kg) and a Control group receiving intravenous infusion of 0.9% normal saline.

A collagenase-injection model of ICH was utilized. Animals were anesthetized for 5 minutes with 5% halothane and endotracheally intubated. Anesthesia was maintained under 1 to 1.5% halothane with ventilation supported using Fi02 of 50%. Tail artery cannulation was applied to monitor the blood pressure and arterial blood gas, and a rectal temperature probe monitored body temperature. The right femoral vein was cannulated and connected to a microinjection infusion pump for TSC or saline administration. Body temperature was maintained at 37° C. with a heating pad. Rats were secured into a stereotactic frame with a midline incision over the skull and a cranial burr hole of 1 mm in diameter was drilled with 0.2 mm anterior and 3.5 mm right lateral to Bregma. A 26-gauge needle was inserted stereotactically into the right basal ganglion (5.5 mm ventral) and 5 μL collagenase (0.05 U bacteria collagenase; type IV, Sigma Chemical Co.) was infused at a rate of 1 μL/min using a microinfusion pump. The needle was kept in the striatum for an additional 5 minutes to limit collagenase flow back into the burr hole. After withdrawing the needle, the craniotomy was sealed with bone wax and the wound was sutured closed.

TSC was injected intravenously 3 hours after ICH at a final total dosage of 0.091 mg/kg. The TSC formulation used was the sterile lyophilized TSC injectable formulation which was reconstituted with sterile water for injection and diluted with deionized water pH'd to 8.0 with dilute sodium carbonate. Normal saline (0.9%) given in the equivalent volume as the TSC dose volume was used as the control vehicle. On random assignment, either TSC or saline was intravenously infused in the animals beginning at 3 hours after collagenase injection. The intravenous dose of TSC administered as an initial bolus injection of 0.1 mL followed by an infusion at a rate of 0.01 mL/min for 60 minutes, and a second bolus injection of 0.1 mL given 30 minutes after the cessation of the infusion. After surgery and dosing, the rats were allowed to recover. Saline-treated animals were used as controls and received the same ICH procedure and saline injections (instead of TSC). The outcomes assessed 48 hours post-ICH included hematoma volume, hemoglobin content representing hemorrhagic volume in the injected striatum, and tissue edema.

Animals were euthanized 48 hours after collagenase infusion by decapitation under deep halothane anesthesia. Brains were dissected and sectioned coronally (2 mm thickness). Using Meta Morph image analysis software, the hemorrhage area for each section was measured and the total hematoma volume was calculated by summing the clot area in each section and multiplying by the thickness of the sections. A tissue edema index was calculated in each rat by measuring and comparing both of the hemispheres (Edema Index=(R−L)×100/L, R is right hemisphere volume, L is left hemisphere volume). A hemorrhagic volume index was quantified by measuring hemoglobin content in the injected hemisphere. Distilled water (1 mL) was added to the ipsilateral cerebral hemisphere collected from each animal, followed by homogenization for 1 minute, sonication on ice with a pulse ultrasonicator for 2 minutes, and centrifugation at 13,000 rpm for 30 minutes. After the hemoglobin-containing supernatant was collected, 800 µL of Drabkin's reagent was added to a 200 µL aliquot and allowed to stand for 15 minutes in the dark. This reaction converts hemoglobin to cyanomethemoglobin, the concentration of which can be assessed by the optical density (OD) of the solution at 550 nm wavelength. Incremental aliquots of blood were obtained from the saline-treated control group by cardiac puncture after anesthesia. This blood was added to freshly homogenized brain tissue obtained from untreated rats to generate a standard absorbance curve.

Results

Hematoma Volume/Size after ICH

The influence of TSC on hematoma volume was assessed in a collagenase-injection model of ICH in male rats. FIG. 6 shows examples of hematomas produced in saline-treated control and TSC-treated rats.

Further assessments demonstrated that TSC does not significantly affect hematoma volume or size after ICH. Hematoma volume was compared between groups of saline-treated (n=6) and TSC-treated (n=6) animals. The hematoma size in the TSC-treated group was slightly, but not statistically significantly, reduced when compared to the control group as shown in FIG. 7. Statistical comparisons between groups showed a p>0.05 which was not statistically significant (n.s.) using the Student's t-test.

Effect of TSC on Hemorrhagic Volume After ICU

TSC-treated animals showed a reduction in hemorrhagic volume after ICH was assessed. Tissue hemoglobin levels were compared between groups of saline-treated control (n=6) and TSC-treated (n=6) animals. Hemorrhagic volume was reduced by approximately 20% in the TSC-treated group. Statistical comparison showed a significant difference (*statistically significant p<0.05) between the 2 groups using the Student's t-test as noted in FIG. 8.

Effect of TSC on Tissue Edema After ICH

The influence of TSC on tissue edema was assessed in the ICH model in rats. Tissue edema was compared between groups of saline-treated control (n=6) and TSC-treated (n=6) animals. Tissue edema was reduced by approximately 45% in the TSC-treated group. Statistical comparison showed a significant difference (*statistically significant p<0.05) between groups using the Student's t-test as presented in FIG. 9.

In this model of hemorrhagic stroke, hematoma volume or size did not differ between TSC- and saline-treated groups demonstrating that TSC does not significantly affect hematoma size after ICH. Hemorrhagic volume as measured in hemoglobin content was reduced by approximately 20% with TSC treatment and this reduction was statistically significant (p<0.05). With TSC treatment, tissue edema was reduced substantially by 45% and was statistically significant (p<0.05). These findings are consistent with the concept that TSC does not aggravate neural injury after ICH, and appears to be beneficial.

Thus, TSC may be given to a stroke victim without first ascertaining if the stroke is an ischemic one or a hemorrhagic one since it produces beneficial effects in both kinds of strokes in these animal models.

REFERENCES

1. Ingall, T., *Stroke—incidence, mortality, morbidity and risk*. J Insur Med, 2004. 36(2): p. 143-52.
2. Lapchak, P. A. and D. M. Araujo, *Advances in ischemic stroke treatment: neuroprotective and combination therapies*. Expert Opin Emerg Drugs, 2007. 12(1): p. 97-112.
3. Group, N. r.-P. S. S., *Tissue plasminogen activator for acute ischemic stroke. The National Institute of Neurological Disorders and Stroke rt-PA Stroke Study Group*. N Engl J Med, 1995. 333(24): p. 1581-7.
4. Lapchak, P. A., D. M. Araujo, and J. A. Zivin, *Comparison of Tenecteplase with Alteplase on clinical rating scores following small clot embolic strokes in rabbits*. Exp Neurol, 2004. 185(1): p. 154-159.
5. Lapchak, P. A., et al., *Neuroprotective effects of the spin trap agent disodium-[(tert-butylimino)methyl]benzene-1, 3-disulfonate N-oxide (generic NXY-059) in a rabbit small clot embolic stroke model: combination studies with the thrombolytic tissue plasminogen activator*. Stroke, 2002. 33(5): p. 1411-5.
6. Lapchak, P. A., et al., *Transcranial near-infrared light therapy improves motor function following embolic strokes in rabbits: An extended therapeutic window study using continuous and pulse frequency delivery modes*. Neuroscience, 2007. 148(4): p. 907-914.
7. Lapchak, P. A., J. Wei, and J. A. Zivin, *Transcranial infrared laser therapy improves clinical rating scores after embolic strokes in rabbits*. Stroke, 2004. 35(8): p. 1985-8.
8. Broderick, J. P., et al., *Finding the most powerful measures of the effectiveness of tissue plasminogen activator in the NINDS tPA stroke trial*. Stroke, 2000. 31(10): p. 2335-41.
9. Clark, W. M., et al., *The rtPA (alteplase) 0- to 6-hour acute stroke trial, part A (A0276g): results of a double-blind, placebo-controlled, multicenter study. Thrombolytic therapy in acute ischemic stroke study investigators*. Stroke, 2000. 31(4): p. 811-6.
10. Lapchak, P. A., *Memantine, an uncompetitive low affinity NMDA open-channel antagonist improves clinical rating scores in a multiple infarct embolic stroke model in rabbits*. Brain Res, 2006. 1088(1): p. 141-7.
11. Lapchak, P. A., *The phenylpropanoid micronutrient chlorogenic acid improves clinical rating scores in rabbits following multiple infarct ischemic strokes: synergism with tissue plasminogen activator*. Exp Neurol, 2007. 205(2): p. 407-13.
12. Lapchak, P. A., et al., *Therapeutic window for nonerythropoietic carbamylated-erythropoietin to improve motor function following multiple infarct ischemic strokes in New Zealand white rabbits*. Brain Res: 2008. 1238: p 208-14.

It will be readily apparent to those skilled in the art that numerous modifications and additions can be made to both the present compounds and compositions, and the related methods without departing from the invention disclosed.

What is claimed is:

1. A method of treating a mammal having a stroke where it is unknown whether the stroke is an ischemic stroke or a hemorrhagic stroke comprising:

i) administering a bipolar trans carotenoid salt having the formula:

YZ-TCRO-ZY, where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, to said mammal;
  ii) determining whether the stroke is an ischemic stroke, and if so determined;
  iii) administering a thrombolytic agent to said mammal, wherein the bipolar trans carotenoid salt is administered within 4 hours of the onset of stroke symptoms and, if the stroke is an ischemic stroke, the thrombolytic agent is administered within 12 hours of the onset of stroke symptoms.

2. A method of treating a mammal showing signs of a hemorrhagic stroke comprising:
  i) administering to said mammal a bipolar trans carotenoid salt having the formula:

YZ-TCRO-ZY, where:
     Y=a cation which can be the same or different,
     Z=a polar group which can be the same or different and which is associated with the cation, and
     TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen.

3. A method as in claim 1, wherein said bipolar trans carotenoid salt is formulated with a cyclodextrin.

4. A method as in claim 1, wherein said bipolar trans carotenoid salt is trans sodium crocetinate (TSC).

5. A method as in claim 1, wherein said thrombolytic agent is tissue plasminogen activator (tPA).

6. A method as in claim 1, wherein said thrombolytic agent is reteplase.

7. A method as in claim 1, wherein said thrombolytic agent is tenecteplase.

8. A method as in claim 1 wherein the bipolar trans carotenoid salt is administered within 3 hours of the onset of stroke symptoms and, if the stroke is an ischemic stroke, the thrombolytic agent is administered within 9 hours of the onset of stroke symptoms.

9. A method as in claim 2, wherein said bipolar trans carotenoid salt is formulated with a cyclodextrin.

10. A method as in claim 4, wherein said TSC is administered by intravenous injection at a dosage of 0.1-2 mg/kg.

11. A method as in claim 4, wherein the thrombolytic agent is administered after administration of TSC and within the first ninety minutes after the onset of stroke symptoms.

12. A method as in claim 4, wherein when said TSC is subjected to Craw and Lambert analysis the absorbency of the highest peak which occurs in the visible wavelength range divided by the absorbency of the highest peak which occurs in the UV wavelength range is greater than 8.

13. A method as in claim 10, wherein when said TSC is subjected to Craw and Lambert analysis the absorbency of the highest peak which occurs in the visible wavelength range divided by the absorbency of the highest peak which occurs in the UV wavelength range is greater than 8.

14. A method as in claim 1, wherein said thrombolytic agent is anistreplase.

15. A method as in claim 1, wherein said thrombolytic agent is streptokinase.

16. A method as in claim 1, wherein said thrombolytic agent is urokinase.

17. A method as in claim 4, wherein said trans sodium crocetinate (TSC) is formulated with gamma cyclodextrin.

18. A method as in claim 17, wherein said thrombolytic agent is tissue plasminogen activator (tPA) and said mammal is human.

19. A method as in claim 3, wherein said bipolar trans carotenoid salt is trans sodium crocetinate (TSC) and said mammal is human.

20. A method as in claim 19, wherein said thrombolytic agent is tissue plasminogen activator (tPA).

21. A method as in claim 4, wherein said thrombolytic agent is tissue plasminogen activator (tPA) and said mammal is human.

* * * * *